United States Patent
Utama et al.

(10) Patent No.: US 12,048,780 B2
(45) Date of Patent: Jul. 30, 2024

(54) BIO-INK FOR 3D PRINTING

(71) Applicant: NewSouth Innovations Pty Limited, New South Wales (AU)

(72) Inventors: Robert Hadinoto Utama, Earlwood (AU); Vincent Tit Guan Tan, Doonside (AU); John Justin Gooding, Queens Park (AU)

(73) Assignee: NewSouth Innovations Pty Limited, New South Wales (AU)

( * ) Notice: Subject to any disclaimer, the term of this patent is extended or adjusted under 35 U.S.C. 154(b) by 686 days.

(21) Appl. No.: 17/261,932

(22) PCT Filed: Jul. 23, 2019

(86) PCT No.: PCT/AU2019/050767
§ 371 (c)(1),
(2) Date: Jan. 21, 2021

(87) PCT Pub. No.: WO2020/019022
PCT Pub. Date: Jan. 30, 2020

(65) Prior Publication Data
US 2021/0299330 A1    Sep. 30, 2021

(30) Foreign Application Priority Data
Jul. 24, 2018 (AU) .............. 2018902674

(51) Int. Cl.
*A61L 27/38* (2006.01)
*A61L 27/26* (2006.01)
(Continued)

(52) U.S. Cl.
CPC ............ *A61L 27/38* (2013.01); *A61L 27/26* (2013.01); *A61L 27/52* (2013.01); *B33Y 70/10* (2020.01);
(Continued)

(58) Field of Classification Search
None
See application file for complete search history.

(56) References Cited

U.S. PATENT DOCUMENTS

2012/0225101 A1    9/2012 Kao et al.
2015/0071997 A1*   3/2015 Garcia ................ A61K 9/5031
                                                    514/23
(Continued)

FOREIGN PATENT DOCUMENTS

JP    H10-197535 A    7/1998
JP    2010-520860 A   6/2010
(Continued)

OTHER PUBLICATIONS

Freudenberg et al., "Glycosaminoglycan-based biohybrid hydrogels: a sweet and smart choice for multifunctional biomaterials," Advanced Materials, 28 (40): 8861-8891 (2016).
(Continued)

*Primary Examiner* — Dominic Lazaro
(74) *Attorney, Agent, or Firm* — Morgan, Lewis & Bockius LLP

(57) ABSTRACT

The technology relates to a 3D printed hydrogel formed from a maleimide containing polymer cross-linked using a bis-thiol containing cross-linking agent having at least two thiol functional groups, processes for preparing the 3D printed hydrogel, and uses thereof.

28 Claims, 3 Drawing Sheets
Specification includes a Sequence Listing.

(51) Int. Cl.
  *A61L 27/52* (2006.01)
  *B33Y 70/10* (2020.01)
  *B33Y 80/00* (2015.01)
  *C12N 5/00* (2006.01)
  *C12N 5/077* (2010.01)
  *C08L 71/02* (2006.01)
  *C08L 89/06* (2006.01)

(52) U.S. Cl.
  CPC ............ *B33Y 80/00* (2014.12); *C12N 5/0012* (2013.01); *C12N 5/0656* (2013.01); *C08L 71/02* (2013.01); *C08L 89/06* (2013.01); *C12N 2500/50* (2013.01); *C12N 2513/00* (2013.01); *C12N 2533/54* (2013.01); *C12N 2537/10* (2013.01)

(56) References Cited

U.S. PATENT DOCUMENTS

| | | |
|---|---|---|
| 2015/0084232 A1 | 3/2015 | Rutz et al. |
| 2019/0106673 A1 | 4/2019 | Skardal |

FOREIGN PATENT DOCUMENTS

| | | |
|---|---|---|
| JP | 2014-533153 A | 12/2014 |
| JP | 2017-501136 A | 1/2017 |
| WO | 2015/172073 A1 | 11/2015 |
| WO | 2016/115410 A1 | 7/2016 |
| WO | WO 2016/179242 A | 11/2016 |
| WO | 2017/011854 A1 | 1/2017 |

OTHER PUBLICATIONS

Phelps et al., "Malemide cross-linked bioactive PEG hydrogel exhibits improved reaction kinetics and cross-linking for cell encapsulation and in-situ delivery," Advanced Materials, 24 (1): 64-2 (2012).
Fu et al., "In Situ forming poly(ethylene glycol)-based hydrogels via thiol-maleimide Michael-type addition," Journal of Biomedical Materials Research A, 98 (2): 201-211 (2011).
Matsumoto et al., "A Water-Based Chitosan-Maleimide Precursor for Bioconjugation: An Example of a Rapid Pathway for an In Situ Injectable Adhesive Gel," Macromolecular Rapid Communications, 37: 1618-1622 (2016).
Holzl et al. "Bioink properties before, during and after 3D bioprinting," Biofabrication, 8 032002 (2016).
Vanderhooft et al., "Synthesis and Characterization of Novel Thiol-Reactive POly(ethylene glycol) Cross-Linkers for Extracellular-Matrix-Mimetic Biomaterials," Biomacromolecules, 8: 2883-2889 (2007).
International Search Report issued in corresponding International Patent Application No. PCT/AU2019/050767 dated Sep. 2, 2019.
Darling, et al., "Controlling the kinetics of thiol-maleimide Michael-type addition gelation kinetics for the generation of homogenous poly(ethylene glycol) hydrogels", Biomaterial, vol. 101, (2016).
Jansen, et al., "Control of thiol-maleimide reaction kinetics in PEG hydrogel networks", ACTA Biomaterialia, vol. 70, (2018).

* cited by examiner

BIO-INK FOR 3D PRINTING

CROSS-REFERENCE TO RELATED APPLICATIONS

This present application is the US national stage of International Patent Application No. PCT/AU2019/050767, filed Jul. 23, 2019, which claims the benefit of and priority to Australian Provisional Patent Application No. AU 2018902674, filed Jul. 24, 2018, the contents of each are hereby incorporated by cross reference in their entireties.

SEQUENCE LISTING

The instant application contains a sequence listing, which has been submitted in XML format via EFS-Web. The contents of the XML copy named "057734-5052_SEQUENCE_LISTING," which was created on Mar. 5, 2024 and is 8,192 bytes in size, the contents of which are incorporated herein by reference in their entirety.

TECHNICAL FIELD

This technology relates broadly to bio-inks for 3D bioprinting. In particular, this technology relates to a 3D printed hydrogel formed from a polymer cross-linked using a cross-linking agent, processes for preparing the hydrogel, and uses thereof.

BACKGROUND

Cells exist three-dimensionally within an extracellular matrix (ECM) in vivo. Interactions between the cells and the ECM play an important role in controlling the biological characteristics and behaviours of cells. In cancer biology, three-dimensional (3D) in vitro cell culture assays are used to culture cells in an environment that closely mimics the native environment of the cells. Such assays maintain the physiological cell-cell and cell-matrix interactions which are absent in two-dimensional monolayer cultures.

3D bioprinting uses 3D printing technology to combine cells and other biomaterials to prepare synthetic structures that mimic the ECM. Commonly, a 3D bioprinter utilises either a drop-on-demand or an extrusion printing technology to print 3D in vitro assays. Although drop-on-demand bioprinting has been reported to maintain high cellular viability upon printing, this technique remains less commonly utilised compared to its extrusion counterpart due to the low viscosity and low cell density of current 3D bio-inks.

Hydrogels, both synthetic and natural, have been used extensively as ECM mimics. In particular, synthetic hydrogels may be highly reproducible and offer excellent control over the physical and cell responsive properties, which are highly desirable of an ECM mimic for in vitro studies. Current approaches for the manual creation of 3D in vitro assays predominantly utilise Matrigel® or collagen as the ECM mimic. Other materials that have been used extensively are hyaluronic acid, chitosan and alginate. As they are sourced from natural products, natural hydrogels are typically biocompatible and, in some cases, carry the necessary biomolecules for cell-matrix interactions. However, natural hydrogels have limitations as ECM mimics as they may be susceptible to batch-to-batch variability, lack physical and biochemical modularity, and/or be difficult to handle.

Various synthetic hydrogels have been prepared in an attempt to overcome the various limitations of natural hydrogels. In particular, covalently cross-linked synthetic hydrogels can provide a more robust and mechanically accurate system than natural hydrogels. However, many of these synthetic hydrogels lack biochemical characteristics that promote cell-matrix interactions. Further, to apply covalently cross-linked synthetic hydrogels to the 3D bioprinting of cells, the materials should be biocompatible in order to allow cells to be printed in situ within the hydrogel. For example, while poly(acrylamide) is a biocompatible synthetic hydrogel used in cell biology (Caliari and Burdick, 2016), the corresponding hydrogel precursor is not biocompatible, thus making it unsuitable for the 3D bioprinting of cells.

Current approaches to 3D bioprinting involve UV-initiated radical cross-linking reactions that allows rapid hydrogel formation (Murphy and Atala, 2014; Donderwinkel et al, 2017: Jungst et al, 2016 Lowe et al, 2014). For example, inkjet printing of photocross-linkable acrylated PEG and peptide was found to be suitable for generating a 3D hydrogel construct for the encapsulation of mesenchymal stem cells (Gao et al, 2017; Gao et al, 2015). However, while the potential use of this approach for 3D bioprinting of living cells has been shown, the use of UV irradiation to initiate photo-cross-linking can cause damage to the DNA in living organisms, while the generated free radicals may also damage sensitive cells.

Advances in 3D bioprinting have been significant in recent years and have the potential to alleviate the limitations of current approaches to 3D in vitro cell culture assays. However, although the benefits of 3D printed cell cultures are well established, utilisation of 3D printed in vitro assays in cell biology is still constrained by their complexity, labour intensive and low-throughput nature. Accordingly, there is a need for alternative ECM mimics for use in 3D bioprinting.

SUMMARY

The present inventors have developed bio-inks suitable for 3D printing that are biocompatible and can form hydrogels rapidly via a substantially non-toxic chemical pathway.

In a first aspect, the present technology provides a 3D printed hydrogel formed from a maleimide containing polymer cross-linked using a bis-thiol containing cross-linking agent having at least two thiol functional groups.

The bis-thiol containing cross-linking agent may comprise more than two thiol functional groups.

In an embodiment, formation of the hydrogel occurs upon combining a solution comprising the maleimide containing polymer (polymer bio-ink) and a solution comprising the bis-thiol containing cross-linking agent (activator) using a 3D printer.

In an embodiment, the 3D printed hydrogel is formed within about 30 minutes or less, or 10 minutes or less, or 1 minute or less, or 30 seconds or less, or 10 seconds or less, or 1 second or less, from the printing of the polymer bio-ink and the activator.

In an embodiment, the polymer bio-ink is biocompatible with cells.

In an embodiment, the activator is biocompatible with cells.

In an embodiment, the polymer bio-ink and the activator when combined during 3D printing form a hydrogel that is biocompatible with cells.

In an embodiment, the maleimide containing polymer is selected from maleimide containing polysaccharides, such as polymers containing fructose, sucrose or glucose monomers; synthetic polymers, such as poly(ethylene glycol) (PEG) maleimide, poly(hydroxyethyl methacrylate (PHEMA) maleimide, poly(E-caprolactone) (PCL) maleimide, poly(vinyl alcohol) (PVA) maleimide, poly(vinylpyrrolidone) (PVP) maleimide, poly(N-isopropylacrylamide) (NIPAAM) maleimide, poly(propylene fumarate) (PPF) maleimide, poly(ethylene imine) (PEI) maleimide, poly(3-methacrylamidopropyl) trimethylammonium (PMAETMA) maleimide, and poly($_L$-lysine) (PLL) maleimide, poly (acrylic acid) (PAA) maleimide, poly(styrene sulfonate) (PSS) maleimide, poly(acrylic acid-stat-dimethylaminoethyl methacrylamide) (P(AA-stat-DMAEMA)) maleimide), and poly(arginine methacrylate) maleimide), or derivatives thereof; maleimide containing biopolymers, such as gelatin maleimide, cellulose maleimide, hyaluronic acid maleimide and alginate maleimide; and maleimide containing nucleobase polymers (i.e., maleimide containing polymers of adenine, thymine, guanine and/or cytosine repeating units); or any combination thereof.

In an embodiment, the maleimide containing polymer comprises a poly(ethylene glycol) (PEG) maleimide.

In an embodiment, the maleimide containing polymer comprises a gelatin maleimide.

In an embodiment, the bis-thiol containing cross-linking agent is selected from synthetic polymers, biopolymers, small molecules, bioactive molecules, or any combination thereof.

In an embodiment, the synthetic polymer is selected from PEG-bis-thiols, poly(N-isopropylacrylamide)-bis-thiols (NIPAAM-bis-thiols), poly(acrylic acid)-bis-thiols, poly (methacrylic acid)-bis-thiols, poly(styrene sulfonate)-bis-thiols, poly(amide)-bis-thiols, or any combination thereof. In an embodiment, the bis-thiol containing cross-linking agent is a PEG-bis-thiol.

In an embodiment, the biopolymers are selected from thiol-gelatin, thiol-cellulose, thiol-chitosan, thiol-hyaluronic acid, or any combination thereof.

In an embodiment, the small molecule is dithiothreitol (DTT).

In an embodiment, the bioactive molecules are selected from short chain peptides with at least two cysteine amino acid groups, inert short chain peptides, enzyme responsive short chain peptides, matrix metalloproteinase (MMP) responsive peptides, or any combination thereof.

In an embodiment, the bis-thiol containing bioactive molecule is selected from an MMP-responsive bis-cysteine peptide.

In an embodiment, the MMP-responsive peptide may be GCIPVSLRSGCG, GCRDGPQGIWGQDRCG, GCRDPLGLDRCG, GCRDEAPLKQDRCG, or any combination thereof.

In an embodiment, the maleimide containing polymer is PEG-maleimide and the bis-thiol containing cross-linking agent is selected from the group consisting of PEG-bis-thiol, an MMP-responsive peptide, and a combination thereof.

In an embodiment, the maleimide containing polymer is PEG-maleimide substituted with at least one bioactive molecule selected from RGD, YIGSR and IKVAV and the bis-thiol containing cross-linking agent is selected from PEG-bis-thiol, an MMP-responsive peptide, or a combination thereof.

In an embodiment, the MMP-responsive peptide is GCIPVSLRSGCG, GCRDPLGLDRCG, or a combination thereof.

In an embodiment, the maleimide containing polymer is gelatin maleimide and the bis-thiol containing cross-linking agent is PEG-bis-thiol.

In an embodiment, the maleimide containing polymer is gelatin maleimide and the bis-thiol containing cross-linking agent is PEG-bis-thiol.

In an embodiment, the molar ratio of maleimide containing polymer to bis-thiol containing polymer is in the range of about 10:1 to about 1:10. The ratio of thiol groups in the bis-thiol containing cross-linker(s) to maleimide groups in the maleimide containing polymer(s) may be greater than about 60%.

The hydrogel may be formed by printing a drop of polymer bio-ink onto a substrate followed by a drop of activator to form a hydrogel droplet, or a drop of activator can be applied to the substrate followed by a drop of polymer bio-ink to form the hydrogel.

Repeating the printing steps forms a hydrogel. During the printing process cells can be included with the polymer bio-ink, the activator, or both polymer bio-ink and activator. Additionally or alternatively, cells may be included with a cell culture medium. The cell culture medium may be included with the polymer bio-ink, the activator, or it may be separate from the polymer bio-ink and the activator. For example, the cell culture medium may be suspended between layers of 3D printed hydrogel formed from the polymer bio-ink and the activator or it may be deposited on a surface of the hydrogel.

In an embodiment, the substrate is selected from any suitable vessel. Examples include microtitre plate of different well configuration (6, 24, 48 and 96-well), microtitre plate with coverslip bottom of different well configuration (6, 24, 48 and 96-well), fluorodish of various sizes, chamber slides of different chamber configuration (1, 2, 4, 8 and 16), cover slip or microscope slides. The vessel may be suitable for containing, holding or growing cells.

In an embodiment, the 3D printed hydrogel further comprises a bioactive molecule. The bioactive molecule may be bound to the maleimide containing polymer, the bis-thiol containing cross-linking agent, or both the maleimide containing polymer and the bis-thiol containing cross-linking agent. Additionally or alternatively, a free bioactive molecule may be present in the 3D printed hydrogel. The free bioactive molecule may be present in the polymer bio-ink, the activator, or both. The bioactive molecule may be selected from a peptide, MMP-responsive peptide, protein, polysaccharide, drug, therapeutic agent, antibody, small molecule inhibitor, kinase inhibitor, phosphatase inhibitor, antigen, pathogen, platelet, growth factor, cytokine, amino acid, nutrient, conditioned media, antibiotic, antiviral, RNA, and any combination thereof. Nanoparticles can also be incorporated into the 3D printed hydrogel.

In an embodiment, the bioactive molecule is selected from CRGDS, CIKVAV, CYIGSR, VEGF with C-terminal unpaired cysteine, protein (e.g., laminin, collagen), and MMP-responsive peptides (e.g., GCIPVSLRSGCG, GCRDGPQGIWGQDRCG, GCRDPLGLDRCG, GCRDEAPLKQDRCG); and any combination thereof.

In an embodiment, the 3D printed hydrogel further comprises a cell culture medium. Examples of suitable culture media include Dulbecco's Modified Eagle Medium (DMEM), Minimum Essential Media (MEM), Iscove's Modified Dulbecco's Medium (IMDM), Media 199, Ham's F10, Ham's F12, McCoy's 5A and Roswell Park Memorial Institute (RPMI) medium. The cell culture medium may be present in the polymer bio-ink, the activator, or both.

In an embodiment, the hydrogel contains cells.

In an embodiment, cells are present in the polymer bio-ink, in the activator, both in the polymer bio-ink and the activator, or in a separate medium prior to 3D printing to allow printing of a hydrogel containing cells.

In an embodiment, cells are suspended within a part of the hydrogel.

In an embodiment, the cells are substantially uniformly suspended throughout the hydrogel.

The concentration of printed cells can be in the range of about $1\times10^5$ to about $5\times10^8$ cells/mL. It will be appreciated that lower or higher concentrations of cells can be printed to form the printed hydrogel containing cells.

In an embodiment, the cells may be selected from liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblast, neural cells, Schwann cells, adipose cells, bone cells, bone marrow cells, cartilage cells, pericytes, mesothelial cells, cells derived from endocrine tissue, stromal cells, stem cells, progenitor cells, lymph cells, blood cells, endoderm-derived cells, ectoderm-derived cells, and mesoderm-derived cells, or any combination thereof. The cells may comprise cancerous cells.

In a second aspect, the present technology provides a method of preparing a 3D printed hydrogel, the method comprising the steps of:
  providing a polymer bio-ink comprising a maleimide containing polymer;
  providing an activator comprising a bis-thiol containing cross-linking agent having at least two thiol functional groups; and
  printing the polymer bio-ink and the activator to form the 3D printed hydrogel.

In an embodiment, the method further comprises providing cells to form a 3D printed hydrogel containing cells. The cells may be present in the polymer bio-ink, in the activator, both in the polymer bio-ink and the activator, or in a separate medium prior to 3D printing.

In an embodiment, the 3D printed hydrogel is formed within 30 minutes or less, or 10 minutes or less, or 1 minute or less, or 30 seconds or less, or 10 seconds or less, or 1 second or less, from the printing of the polymer bio-ink and the activator.

In an embodiment, the polymer bio-ink, the activator, or both are adjusted to about pH 7.4 prior to printing.

In an embodiment, the pH is adjusted using NaOH.

The method can be used to prepare the 3D printed hydrogel according to the first aspect.

In a third aspect, the present technology provides a kit for 3D printing, the kit comprising:
  a polymer bio-ink comprising a maleimide containing polymer; and
  an activator comprising a bis-thiol containing cross-linking agent having at least two thiol functional groups.

In an embodiment, the kit further comprises cells.

In an embodiment, the kit further comprises a printing substrate.

In a fourth aspect, the present technology provides a cell assay comprising a 3D printed hydrogel containing cells according to the first aspect.

In a fifth aspect, the present technology provides use of a 3D printed hydrogel containing cells according to the first aspect for a cell assay.

DEFINITIONS

The following are some definitions of terms used in the art that may be helpful in understanding the description. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

As used herein, the term "about" means±10% of the recited value.

As used herein, the terms "cross-linker" and "cross-linking agent" are used interchangeably and mean a chemical compound that is capable of covalently cross-linking a maleimide containing polymer. The cross-linking agent of the present technology comprises at least two thiol functional groups, referred to herein as a "bis-thiol containing cross-linker" or "bis-thiol containing cross-linking agent". The bis-thiol containing cross-linking agent may comprise more than two thiol functional groups, e.g., three, four, five, six or more thiol functional groups.

As used herein, the term "polymer bio-ink" refers to a solution, preferably an aqueous solution, comprising a maleimide containing polymer, or a combination of two or more maleimide containing polymers. As used herein, the term "activator" refers to a solution, preferably an aqueous solution, comprising at least one bis-thiol containing cross-linking agent. When the polymer bio-ink and the activator of the present technology are mixed, i.e., during 3D printing, a thiol-maleimide cross-linking reaction occurs to form a hydrogel.

As used herein, the term "biocompatible" in relation to a substance means that substance is substantially non-toxic to living cells or tissue.

As used herein, the term "bioactive molecule" refers to molecules having biological activity that can be used with cultured cells.

As used herein, the term "cell polymer bio-ink" refers to cells mixed with polymer bio-ink comprising at least one maleimide containing polymer. As used herein, the term "cell activator" refers to a cells mixed with an activator comprising at least one bis-thiol containing cross-linking agent. Cell polymer bio-inks and cell activators of the present technology may be aqueous solutions of one or more types of bioactive molecules in which cells are suspended, and can remain suspended, throughout the 3D bioprinting process.

The term "cell culture medium" refers to a liquid that can be used to store, maintain, grow or culture cells.

As used herein, the term "drop-on-demand" in relation to 3D bioprinting refers to a printing process whereby the delivery of bio-ink is based on the generation of discrete droplets. Drop-on-demand bioprinting may include, but is not limited to, thermal inkjet, piezo inkjet and microvalve based bioprinting.

Where a range of values is given throughout the description and claims of this specification, the recited range is intended to include any value within that range.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "consisting of" means "consisting only of", that is, including and limited to the stated element(s), integer(s) or step(s), and excluding any other element(s), integer(s) or step(s). The term "consisting essentially of" means the inclusion of the stated element(s), integer(s) or step(s), but other element(s), integer(s) or step(s) that do not materially alter or contribute to the working of the invention may also be included.

In order that the present technology may be more clearly understood, preferred embodiments will be described with reference to the following drawings and examples.

DETAILED DESCRIPTION OF EMBODIMENTS

Figure 1:
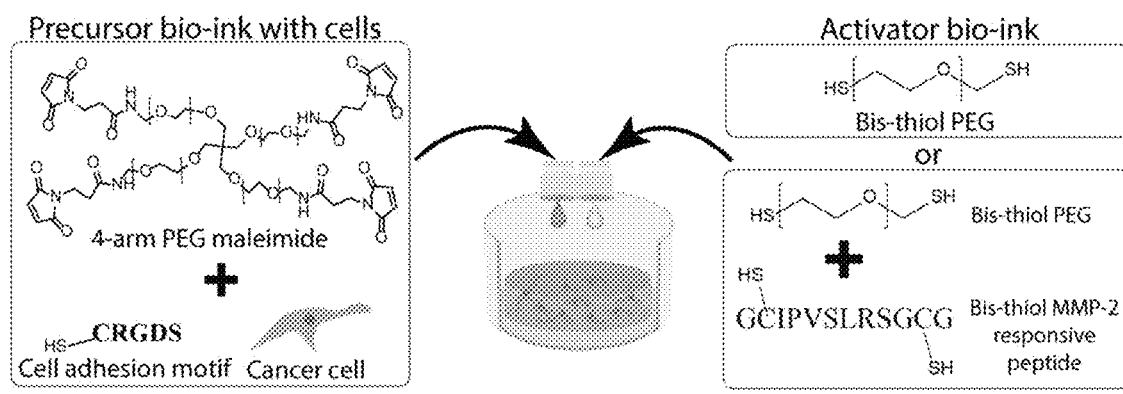
FIG. 1 is a representative schematic of the 3D bioprinting process.

The present technology relates to 3D printed hydrogels. The 3D printed hydrogels may be capable of supporting cell viability for a prolonged duration. The hydrogels of the present technology are prepared by 3D printing of a polymer bio-ink and an activator that are biocompatible and rapidly form hydrogels upon printing, allowing for high-throughput production of 3D cell structures and assays.

In particular, the present inventors have found that maleimide containing polymers covalently cross-linked using a bis-thiol containing cross-linking agent allow for rapid formation of uniform hydrogels via a biocompatible crosslinking pathway under physiological conditions without the aid of any co-reactants and do not produce any toxic by-products. Thus, the 3D printed hydrogels of the present technology are formed by combining a polymer bio-ink comprising a maleimide containing polymer and an activator comprising a bis-thiol containing cross-linker having at least two thiol functional groups.

Polymer Bio-Ink

The polymer bio-ink of the present technology comprises a maleimide containing polymer, or a combination or two or more maleimide containing polymers. The maleimide containing polymer(s) may be any polymer(s) containing maleimide reactive groups to form a hydrogel. Polymer(s) containing free maleimide groups may also be present in the hydrogel.

Maleimide containing polymers of various molecular masses, molecular architectures, molecular distribution and functionalities may be used in the polymer bio-ink. For example, the molecular mass of the maleimide containing polymer(s) may be in the range of about 1 kDa to about 10,000 kDa, or about 5 kDa to about 10,000 kDa, or about 5 kDa to about 5,000 kDa, or about 5 kDa to about 1,000 kDa, or about 10 kDa to about 1,000 kDa, or about 20 kDa to about 1,000 kDa, or about 10 kDa to about 500 kDa. The maleimide containing polymer(s) may have any suitable molecular architecture, for example, linear, block, branched, star, ring, comb, or brush polymer(s), among others, or any combination thereof. The molecular distribution, which refers to the distribution of monomeric units along the polymer backbone, may include homo, block, statistical, random, or multi-block distribution, among others, or any combination thereof. The functionality (i.e., the type of monomers), may include, but are not limited to hydroxyl, amine, thiol carboxylic acid, alkene, alkyne and multi-membered carbon rings, among others. The polymers may contain one functionality, or two or more functionalities (i.e., copolymers).

In an embodiment, the maleimide containing polymer is biocompatible.

The maleimide containing polymer(s) are prepared synthetically by incorporating two or more maleimide reactive groups into the polymer. The two or more maleimide groups may be incorporated into the polymer(s) by any suitable method known in the art, for example, carbodiimide coupling, Steglich esterification and thiol-maleimide coupling with excess bis-maleimide molecule. Additionally or alternatively, commercially available maleimide containing polymer(s) may be used.

Non-limiting examples of suitable maleimide containing polymers for use in the polymer bio-ink of the present technology include: maleimide containing polysaccharides, such as polymers containing fructose, sucrose or glucose monomers; synthetic polymers, such as poly(ethylene glycol) (PEG) maleimide, poly(hydroxyethyl methacrylate (PHEMA) maleimide, poly(E-caprolactone) (PCL) maleimide, poly(vinyl alcohol) (PVA) maleimide, poly(vinylpyrrolidone) (PVP) maleimide, poly(N-isopropylacrylamide) (NIPAAM) maleimide, poly(propylene fumarate) (PPF) maleimide, poly(ethyleneimine) (PEI) maleimide, poly(3-methacrylamidopropyl) trimethylammonium (PMAETMA) maleimide, poly($_L$-lysine) (PLL) maleimide), poly(acrylic acid) (PAA) maleimide, poly(styrene sulfonate) (PSS) maleimide), poly(acrylic acid-stat-dimethylaminoethyl methacrylamide) (P(AA-stat-DMAEMA)) maleimide, and poly(arginine methacrylate) maleimide, or derivatives thereof; maleimide containing biopolymers, such as gelatin maleimide, cellulose maleimide, hyaluronic acid maleimide and alginate maleimide; and maleimide containing nucleobase polymers (i.e., maleimide containing polymers of adenine, thymine, guanine and/or cytosine repeating units); or any combination thereof.

PEG is a particularly attractive material for the preparation of synthetic hydrogels as ECM mimics because it is commercially available, inert, non-toxic in biological applications, and versatile towards various chemical modifications. Further, PEG-based polymer bio-inks may have low relative viscosity due to the low molecular weight of the PEG polymeric precursors, making them particularly suitable for drop-on-demand bioprinting. Thus, in an embodiment, the maleimide containing polymer is a poly(ethylene glycol) (PEG) polymer containing at least two maleimide reactive groups (PEG-maleimide). The PEG-maleimide may have any suitable molecular architecture including, but not limited to, 3-arm PEG-maleimide, 4-arm PEG-maleimide, block-copolymers of PEG with at least two maleimide groups, or any combination thereof. The PEG group may have any suitable molecular weight. For example, the molecular mass of the PEG group may be in the range of about 1 kDa to about 50 kDa, or about 1 kDa to about 40 kDa, or about 1 kDa to about 30 kDa, or about 5 kDa to about 30 kDa, or about 5 kDa to about 20 kDa, or about 5 kDa to about 10 kDa, or about 10 kDa to about 20 kDa. In an embodiment, the molecular mass of the PEG groups is about 5 kDa, or about 10 kDa, or about 20 kDa.

The term "3-arm PEG-maleimide" refers to a polymeric compound having the following structure (n=38-3,788):

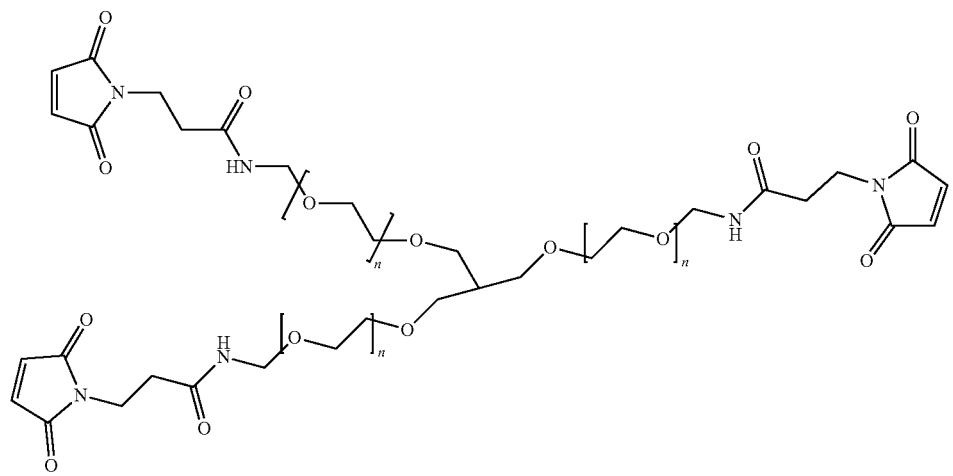

The term "4-arm PEG-maleimide" refers to a polymeric compound having the following structure (n=28-2,841):

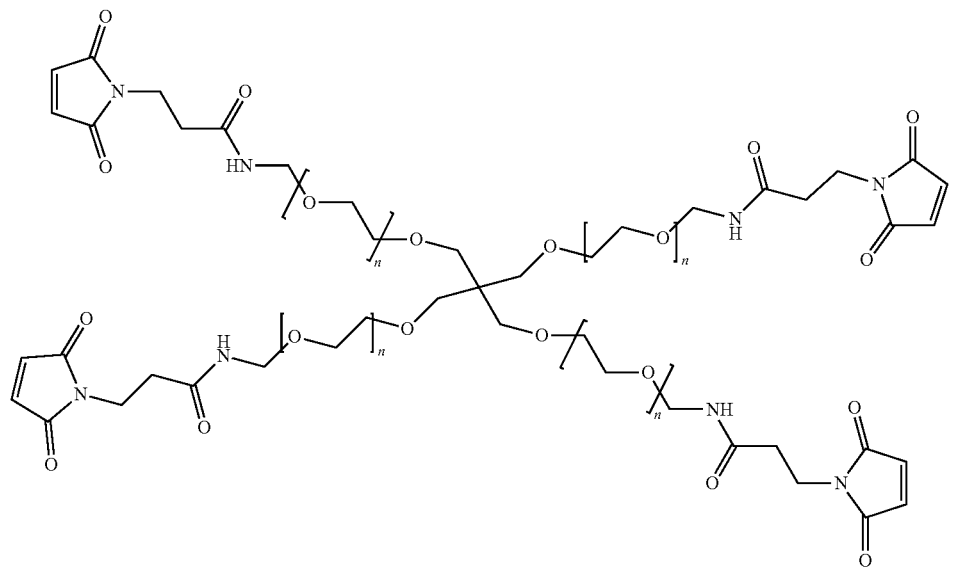

The properties of the maleimide containing polymers may be tailored for specific applications by partially modifying the maleimide group(s) with one or more functional groups or other moieties. Partial modification means that at least one, preferably at least two, maleimide groups remains intact for cross-linking with the bis-thiol containing cross-linker. Accordingly, if a bioactive molecule is to be incorporated into a maleimide containing polymer, the maleimide containing polymer contains at least two, and typically at least three, maleimide groups. This approach allows for the reproducibility and modularity of the polymers to be maintained, while introducing relevant biological characteristics into the 3D printed hydrogel. Thus, in an embodiment, the maleimide groups of the maleimide containing polymer may be partially modified with one or more bioactive molecules.

The polymer bio-ink of the present technology may be prepared as an aqueous solution comprising the maleimide containing polymer in any suitable formulation known in the art. For example, the polymer bio-ink may be prepared as an aqueous formulation comprising at least one maleimide containing polymer and, optionally, one or more bioactive molecules. For example, the aqueous formulation may be a solution comprising a maleimide containing polymer in a pH buffered solution or a cell culture medium. In some embodiments the polymer bio-ink may comprise two maleimide containing polymers in any ratio, for example, in a ratio between about 10:1 to about 1:10, e.g., about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10.

In an embodiment, the polymer bio-ink is provided in the form of an aqueous solution comprising the maleimide containing polymer. Typically, the polymer bio-ink is prepared by dissolving a maleimide containing polymer in the solution, preferably a cell culture medium. In some embodiments, the polymer bio-ink may comprise a mixture of two or more maleimide containing polymers. The polymer bio-ink may contain any suitable concentration of maleimide containing polymer(s) in the solution. For example, the concentration of maleimide containing polymer(s) in the polymer bio-ink solution may be in the range of about 1 wt % to 50 wt %, or about 1% to 40 wt %, or about 1 wt % to 30 wt %, about 5 wt % to 20 wt %, about 5 wt % to 15 wt %, or about 10 wt % to 20 wt %. The polymer bio-ink may comprise one or more bioactive molecules covalently bound to a maleimide containing polymer. Additionally or alternatively, the polymer bio-ink may comprise one or more free bioactive molecules in solution. The concentration of bioactive molecule(s) in the polymer bio-ink may be in the range of about 0.1 mM to 10 mM, about 0.5 mM to 10 mM, about 1 mM to 10 mM, about 1 mM to 5 mM, about 2 mM to 5 mM or about 2 mM to 3 mM.

In an embodiment, the polymer bio-ink is prepared as a sterile solution. Suitable methods for preparing sterile solutions, or methods of sterilising the polymer bio-ink solutions, will be known to those skilled in the art.

In an embodiment, the polymer bio-ink is biocompatible.

Activator

The activator of the present technology comprises a bis-thiol containing cross-linker. The bis-thiol containing cross-linker may be any compound containing at least two thiol groups, referred to herein as a bis-thiol. Preferably, the thiol groups are terminal thiol groups.

In an embodiment, the bis-thiol containing cross-linker is biocompatible.

In an embodiment, the bis-thiol containing cross-linker may be a bis-thiol containing polymer, preferably a terminal bis-thiol containing synthetic polymer. Suitable bis-thiol containing synthetic polymers include, but are not limited to, PEG-bis-thiols, poly(N-isopropylacrylamide)-bis-thiols (NIPAAM-bis-thiols), poly(acrylic acid)-bis-thiols, poly (methacrylic acid)-bis-thiols, poly(styrene sulfonate)-bis-thiols, poly(amide)-bis-thiols, or any combination thereof. Alternatively, the bis-thiol containing cross-linker may be a bis-thiol containing biopolymer, preferably a terminal bis-thiol containing biopolymer. Suitable bis-thiol containing biopolymers include, but are not limited to, thiol-gelatin (e.g., of bovine, porcine and cold fish origin), thiol-hyaluronic acid (e.g., from *Streptococcus equi*, bovine and human umbilical cord), or any combination thereof.

In an embodiment, the bis-thiol containing cross-linker is a PEG-bis-thiol. The PEG-bis-thiol may have any suitable molecular architecture including, but not limited to, linear, branched and star PEG architectures, among others. In an embodiment, the PEG-bis-thiol is a linear PEG-bis-thiol. The molecular mass of the PEG group may vary, for example, the molecular mass of the PEG group may be in the range of about 1 kDa to about 50 kDa, or about 1 kDa to about 40 kDa, or about 1 kDa to about 30 kDa, or about 5 kDa to about 30 kDa, or about 5 kDa to about 20 kDa, or about 5 kDa to about 10 kDa, or about 10 kDa to about 20 kDa. In an embodiment, the molecular mass of the PEG groups is about 5 kDa, or 10 about kDa, or about 20 kDa.

An example of a linear PEG-bis-thiol has the following structure (n=11-1,136):

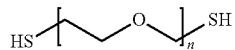

In some embodiments, the bis-thiol containing cross-linker may be a bis-thiol containing small molecule. Suitable bis-thiol containing molecules include, but are not limited to, dithiothreitol (DTT) (used with or without sodium borate or borax), or any combination thereof. In other embodiments the bis-thiol containing cross-linker may be a bis-thiol containing short chain peptide with at least two cysteine amino acid groups, preferably terminal cysteine groups (i.e., a thiol flanked amino acid sequence). Suitable bis-thiol containing short chain peptides flanked with two cysteine amino acid groups include, but are not limited to, inert short chain peptide sequences, enzyme responsive short chain peptides (e.g., MMP-responsive, serine responsive, cysteine responsive, aspartic responsive, glutamic responsive, caspase responsive or trypsin responsive peptide sequences), or any combination thereof.

In an embodiment, the bis-thiol containing cross linker is a bis-thiol containing bioactive molecule. For example, the bis-thiol containing short chain peptide may be an MMP-responsive bis-cysteine peptide. For example, the MMP-responsive peptide may be an MMP-2 responsive bis-cysteine peptide (e.g., GCIPVSLRSGCG), an MMP-1, -2, -3, -7, -8 and -9 responsive bis-cysteine peptide (e.g., GCRDGPQGIWGQDRCG), MMP-15 responsive thiolated peptide (e.g. GCRDEAPLKQDRCG) or MMP-1, -2, -3, -7, -8, -9, -12, -13 and -14 responsive bis-cysteine peptide (e.g., GCRDPLGLDRCG).

The activator may comprise a combination of two or more types of bis-thiol containing cross-linkers in any ratio. For example, the activator may comprise a combination of two types of bis-thiol containing cross-linkers in a ratio between about 10:1 to about 1:10, e.g., about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10.

In an embodiment, the activator may be in the form of an aqueous solution comprising a bis-thiol containing cross-linker. The aqueous solution may be a cell culture medium. In some embodiments, the activator may comprise a mixture of two or more bio-thiol containing cross-linkers. The activator may contain any suitable concentration of bis-thiol containing cross-linker(s) in the solution. In preferred embodiments, the concentration of bis-thiol containing cross-linker(s) in the activator is equal to or less than the concentration of maleimide containing polymer(s) in the complementing polymer bio-ink. The molar ratio of maleimide containing polymer(s) to bis-thiol containing cross-linker(s) may be in the range of about 10:1 to 1:1, about 9:1 to 1:1, about 8:1 to 1:1, about 7:1 to 1:1, about 6:1 to 1:1, about 5:1 to 1:1, about 4:1 to 1:1, about 3:1 to 1:1, or about 2:1 to 1:1. The bis-thiol containing cross-linking agent may include a bioactive molecule, or it may comprise one or more bioactive molecules covalently bound to it. Additionally or alternatively, the activator may comprise one or more free bioactive molecules in solution. The concentration of bioactive molecule(s) in the activator may be in the range of about 0.1 mM to 10 mM, about 0.5 mM to 10 mM, about 1 mM to 10 mM, about 1 mM to 5 mM, about 2 mM to 5 mM or about 2 mM to 3 mM.

In an embodiment, the activator is a sterile solution. Suitable methods for preparing sterile solutions, or method of sterilising the activator solutions will be known to those skilled in the art.

The formulation of the activator may the same the formulation of the polymer bio-ink, or it may be different. In preferred embodiments, the formulation used for the polymer bio-ink and activator are the same.

In an embodiment, the activator is biocompatible.

3D Printed Hydrogel

The 3D printed hydrogel of the present technology comprises a maleimide containing polymer cross-linked using a bis-thiol containing cross-linking agent. In an embodiment, the 3D printed hydrogel contains cells.

In an embodiment, the 3D printed hydrogel is prepared by 3D printing of a polymer bio-ink comprising the maleimide containing polymer and an activator comprising the bis-thiol containing cross-linking agent.

In order to be suitable for use in 3D bioprinting, formation of a hydrogel should occur rapidly. However, rapid formation of hydrogels used in the prior art typically resulted in the formation of irregular hydrogels. Current approaches to controlling the rate of cross-linking and producing a uniform gel in 3D bioprinting involve the utilisation of external driving forces, such as UV irradiation and co-reactants or catalysts. These external drivers do not participate in the formation of the hydrogel but rather assist in the formation of the hydrogel, and may affect the cellular and biological characteristics of the cells encapsulated in the hydrogel. In particular, a photochemical cross-linking reaction involving the use of UV irradiation may involve the use of a free radical source that must be removed from the product so that it does not interact with cells in the hydrogel.

The present inventors have surprisingly found that rapid formation of uniform hydrogels capable of supporting cells at high density and viability can be achieved by reacting a maleimide containing polymer with a bis-thiol containing cross-linker. Maleimide groups react rapidly and spontaneously with thiols under physiological conditions. As this reaction does not require any external driving forces, it is particularly attractive for use in 3D bioprinting of in vitro assays as it eliminates the needs for potentially cytotoxic co-reactants, radical initiators or UV irradiation. In addition, no unwanted or cytotoxic by-products are produced, allowing for in situ printing of cells without producing unwanted by-products.

The cross-linking reaction between the maleimide containing polymers using the bis-thiol containing cross-linking agent occurs rapidly upon contact of the polymer bio-ink with the activator, allowing for rapid formation of the 3D printed hydrogel. Accordingly, in some embodiments, the hydrogel is formed within 30 minutes or less from the printing of the polymer bio-ink and the activator. For example, the hydrogel may form within 30 minutes or less, or 20 minutes or less, or 10 minutes or less, or 1 minute or less, or 30 seconds or less, or 10 seconds or less, or 1 second or less, from the printing of the polymer bio-ink and the activator. Various factors, such as the size, shape, composition, among others, may affect the rate of formation of the 3D printed hydrogel.

An exemplary reaction between a maleimide containing polymer and a bis-thiol containing cross-linker is illustrated below in Scheme 1. The reaction involves nucleophilic (Michael) addition of a thiol group on the bis-thiol containing cross-linker (1) with the alkene functional group of a maleimide moiety on the maleimide containing polymer (2) to produce a 3-substituted succinimide group under aqueous conditions (e.g., in a cell culture medium). This reaction is particularly useful for 3D bioprinting of in vitro assays because it eliminates the needs for potentially cytotoxic co-reactants, radical initiators or UV irradiation. Further, covalent cross-linking occurs rapidly and spontaneously upon mixing of the maleimide containing polymer and the bis-thiol cross-linker under physiological conditions (e.g., at a pH of about 6.5-7.5, preferably pH 7.4) to produce cross-linked polymer (3).

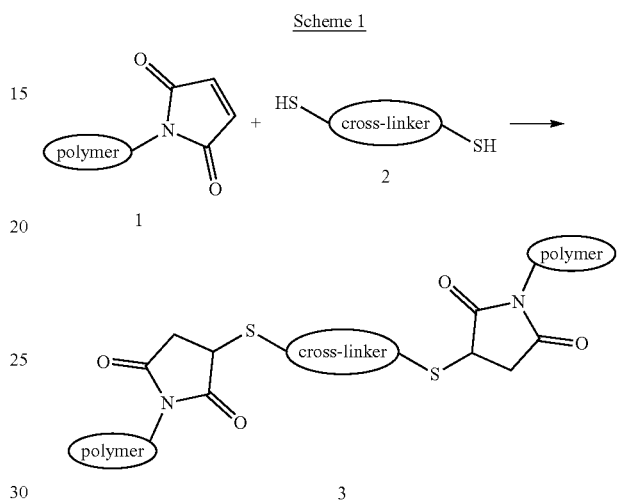

In an embodiment, the pH of the polymer bio-ink, the activator, or both may be adjusted to physiological pH (e.g., about 6.5-7.5, preferably about pH 7.4) prior to 3D printing using a suitable base. Suitable bases will be apparent to those of ordinary skill in the art.

In an embodiment, the base is NaOH.

The present inventors have found that the use of NaOH to adjust the pH of the polymer bio-ink, the activator may accelerate gelation during 3D printing, allowing for rapid formation of the 3D printed hydrogel (e.g., less than about 1 second). Further, the inventors have found that the presence of NaOH may reduce cell aggregation in the polymer bio-ink, activator, or both, allowing for high concentrations of cells to be dispersed in solution for 3D printing through a small nozzle orifice.

In an embodiment, the molar ratio of maleimide containing polymer is greater than the bis-thiol containing cross-linker, such that the bis-thiol containing cross-linker is consumed. The resulting hydrogel may comprise the cross-linked product and excess maleimide containing polymer (if any) without any additional unwanted by-products. For example, the molar ratio of maleimide containing polymer(s) to bis-thiol containing cross-linker(s) may be in the range of about 10:1 to 2:1, about 9:1 to 2:1, about 8:1 to 2:1, about 7:1 to 2:1, about 6:1 to 2:1, about 5:1 to 2:1, about 4:1 to 2:1, about 3:1 to 2:1.

Preferably, for hydrogel formation, the number of thiol groups in the bis-thiol containing cross-linker(s) is greater than about 60% of the number of maleimide groups in the maleimide containing polymer(s). For example, the number of thiol groups in the bis-thiol containing cross-linker(s) to maleimide groups in the maleimide containing polymer(s) may be about 60%, or 70%, or 80%, or 90%, or 100%, or 200% or greater. In some embodiments, the number of thiol groups in the bis-thiol containing cross-linker(s) is the same as (i.e., 100% of) the number of maleimide groups in the maleimide containing polymer(s).

As the polymer bio-inks and activators disclosed herein may be used to produce large quantities of assays, the materials used for the preparation of the polymer bio-inks and activators are preferably readily commercially available in bulk, or readily prepared from such commercially available materials.

A typical process for preparing a 3D printed hydrogel of the present technology may comprise the steps of:
providing a polymer bio-ink comprising a maleimide containing polymer;
providing an activator comprising a bis-thiol containing cross-linking agent; and
3D printing the polymer bio-ink and the activator to form the 3D printed hydrogel.

In an embodiment, the process further comprising providing cells, such that 3D printing of the polymer bio-ink, the activator and the cells forms a 3D printed hydrogel containing cells.

In an embodiment, cells are suspended in the hydrogel. The cells may be provided in the polymer bio-ink, the activator, or both, or in another medium. Cells may be suspended in a part (or multiple parts) of the hydrogel, or they may be substantially uniformly suspended throughout the hydrogel.

In an embodiment, cells are provided in a cell culture medium. The cell culture medium may be included within the polymer bio-ink, the activator, or it may be provided separately from the polymer bio-ink and the activator. For example, the cell culture medium may be suspended between layers of 3D printed hydrogel formed from the polymer bio-ink and the activator or it may be deposited on a surface of the hydrogel.

In an embodiment, the 3D printed hydrogel further contains a bioactive molecule. The bioactive molecule may be provided in the polymer bio-ink or the activator, or both. The bioactive molecule may be freely suspended in the polymer bio-ink or activator, or both, or it may be bound to the maleimide containing polymer and/or the bis-thiol containing cross-linker.

In an embodiment the 3D printing process is carried out in a substantially sterile environment.

Bioactive Molecules

The 3D printed hydrogel of the present technology may be modified by one or more bioactive molecules to introduce certain biological characteristics. For example, the biological characteristics of the 3D printed hydrogel may be modified by incorporating a protein, peptide (e.g., MMP-responsive peptide), chemoattractant, growth factor, organic dyes, fluorescent dyes, drug, therapeutic agent, antibody, small molecule inhibitor, kinase inhibitor, phosphatase inhibitor, antigen, pathogen, platelet, cytokine, nutrients (e.g., mono- and poly-saccharides), conditioned media, antibiotic, antiviral, RNA and relevant variants (e.g., siRNA, mRNA), among others. One or more bioactive molecules may be incorporated into the 3D printed hydrogel by covalent bonding to the maleimide containing polymer, the bis-thiol containing cross-linker, or any combination thereof. Nanoparticles can also be incorporated into the 3D printed hydrogel.

In an embodiment the bioactive molecule is a short chain peptide (e.g., Arg-Gly-Asp (RGD) containing a cysteine (C) amino acid on either the N or C terminus), a growth factor (e.g., VEGF), a protein (e.g., laminin, collagen), or a chemoattractant (e.g., stromal cell-derived factor-1 (CXCL12)), or any combination thereof. Other suitable bioactive molecules will be known to those skilled in the art.

In some embodiments, one or more bioactive molecules may be incorporated into the 3D printed hydrogel by incorporating the free bioactive molecule(s) into the polymer bio-ink, the activator, or both. The polymer bio-ink, the activator, or both, may comprise a cell culture medium.

In an embodiment, the bioactive molecules may be bound to the maleimide containing polymer. Bioactive molecules may be introduced into a maleimide containing polymer by reaction of the maleimide group with the bioactive molecule to form a covalent bond. For example, a covalent bond may form by a Michael-type addition reaction between thiols and vinyl-carrying bioactive molecules (e.g., in aqueous media), a Schiff base reaction between amino and aldehyde groups, a Diels-Alder reaction, click chemistry, aminolysis reaction to active ester group, or enzyme cross-linking. Thiol moieties are abundant in many bioactive molecules, therefore incorporation of a bioactive molecule into the maleimide containing polymer may occur by nucleophilic (Michael) addition of a thiol group to the alkene moiety of the maleimide group to produce a 3-substituted succinimide moiety. Depending on the conditions and mole ratio of reactants used, the resulting compound will have at least one maleimide group converted to a 3-substituted succinimide group bearing the bioactive molecule, leaving at least one, preferably at least two, maleimide groups intact. A skilled person will be able to determine the appropriate conditions (e.g., molar ratio of reactants) to control the reaction to ensure that at least one, or at least two or more, maleimide group remains intact.

In a typical process for incorporating a thiol-containing bioactive molecule into the maleimide containing polymer, the bioactive molecule and maleimide containing polymer are mixed at room temperature in aqueous solution (e.g., buffer or cell culture medium) at a molar ratio in which the maleimide containing polymer exceeds that of the bioactive molecule (e.g., 3:1, or 4:1, or 5:1). The completion of the reaction may be monitored, for example, via Ellman's assay, to confirm that no free thiol groups remain. A typical reaction time is about 30 minutes. After completion of the reaction, a suitable base (e.g., NaOH) may be added if necessary to adjust the pH of the solution to physiological pH (about 7.4). Suitable bases for adjusting the pH to physiological pH will be apparent to those of ordinary skill in the art. The resulting modified maleimide containing polymer solution can be used without the need for isolation or purification.

In an embodiment, the pH of the biomolecule-containing polymer bio-ink or activator solution is adjusted to physiological pH (e.g., about 6.5-7.5, preferably pH 7.4) using NaOH. Use of NaOH to adjust the pH of the polymer bio-ink or activator may allow for rapid polymerisation during subsequent 3D printing, thereby accelerating hydrogel formation (e.g., less than 1 second). Further, the use of NaOH may reduce cell aggregation in the polymer bio-ink, activator, or both, allowing for high concentrations of cells to be dispersed in solution for 3D printing through a small nozzle orifice.

An example of a 4-arm PEG-maleimide partially modified with RGD (4-arm PEG-maleimide-RGD) has the following structure (n=28-2,841), prepared by reacting 4-arm PEG-maleimide with CRGDS at a 4:1 molar ratio:

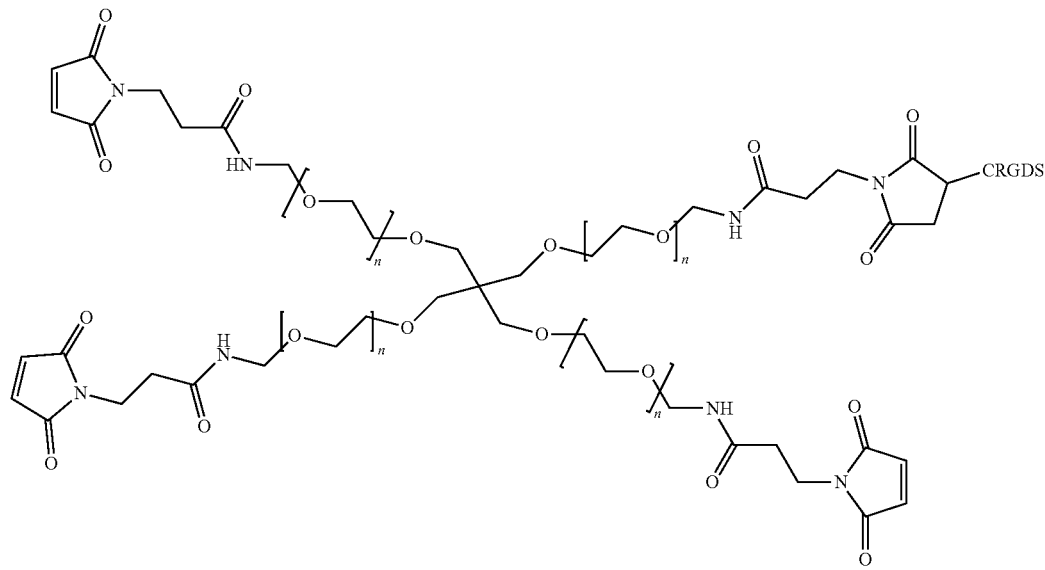

An example of a 4-arm PEG-maleimide partially modified with VEGF (4-arm PEG-maleimide-VEGF) has the following structure (n=28-2,841), prepared by reacting 4-arm PEG-maleimide with VEGF at a 4:1 molar ratio:

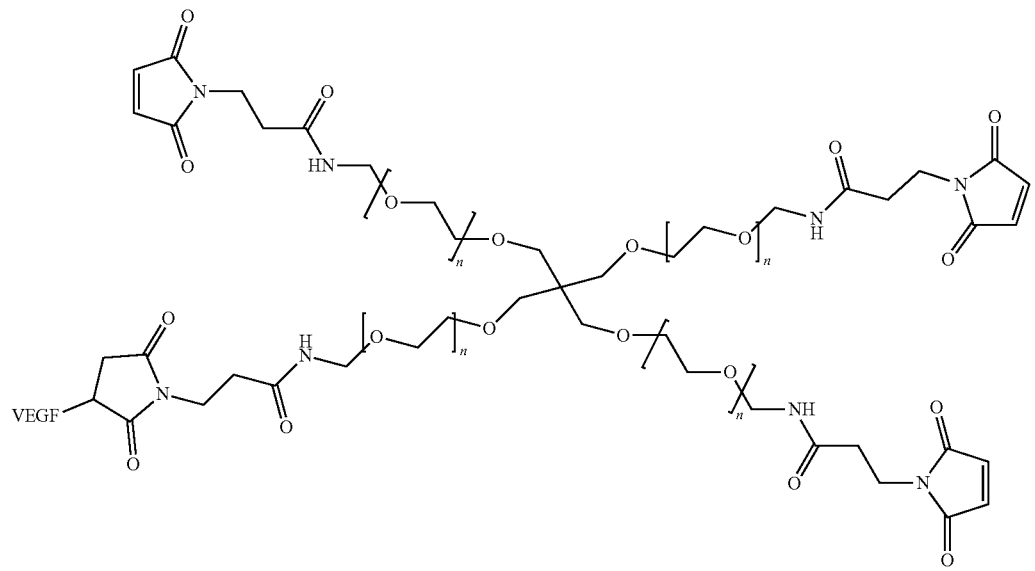

In some embodiments, a bioactive molecule such as CRGDS CIKVAV, VEGF with C-terminal unpaired cysteine and/or MMP-responsive peptide (e.g., GCIPVSLRSGCG, GCRDGPQGIWGQDRCG. GCRDPLGLDRCG or GCRDEAPLKQDRCG) are incorporated into the 3D printed hydrogel to introduce biological functionalities. For example, cellular attachment may be introduced through the incorporation of the CRGDS or CIKVAV cell adhesive motif, angiogenesis may be promoted by the introduction of VEGF, and cell motility may be promoted by incorporation of MMP-responsive peptide cross-linkers. GCIPVSLRSGCG is particularly suitable for use as the bis-thiol containing cross linker in the cross-linking agent, but may additionally or alternatively be covalently linked to the maleimide containing polymer, the bis-thiol containing cross-linker, or both, or added as the free bioactive molecule to the polymer bio-ink, activator or both.

The bioactive molecule may be present in the 3D printed hydrogel at any suitable concentration to achieve the desired biological characteristics. For example, the bioactive molecules may be present in the 3D printed hydrogel at a concentration in the range of about 1 nM to 100 µM, about 1 nM to 50 µM, about 5 nM to 50 µM, about 10 nM to 50 µM, about 50 nM to 50 µM, about 100 nM to 50 µM, about 100 nM to 1 µM, or about 500 nM to 1 µM.

Cells

Cells may be incorporated into the 3D printed hydrogels of the present technology. Cell culture media may also be incorporated into the hydrogels to maintain cell viability or encourage growth and cell division. The cells and/or cell culture media may be incorporated into the hydrogel by incorporating them into the polymer bio-ink or the activator, or both.

In an embodiment, cells are provided in the polymer bio-ink, the activator, both the polymer bio-ink and the activator, or in a separate medium.

The polymer bio-ink and/or the activator may include a cell culture medium. The cell culture medium may be selected from any suitable media that are compatible with the cells and maintains the viability of the cells during the 3D printing process. For example, the cell culture medium may be a solution comprising water (e.g., sterilised MilliQ water), a buffer and a cell culture medium. Suitable buffers include, but are not limited to phosphate buffered saline (PBS), 2-[4-(2-hydroxyethyl)piperazin-1-yl]ethanesulfonic acid (HEPES) and 2-(cyclohexylamino)ethanesulfonic acid (CHES), or any combination thereof. Non-limiting examples of suitable cell culture media include Dulbecco's Modified Eagle Medium (DMEM), Minimum Essential Media (MEM), Iscove's Modified Dulbecco's Medium (IMDM), Media 199, Ham's F10, Ham's F12, McCoy's 5A and Roswell Park Memorial Institute (RPMI) medium.

In some embodiments, the cell culture medium may further comprise reducing agents (e.g., 2-mercaptoethanol or tris(2-carboxyethyl)phosphine (TCEP)), stabilizing agents (e.g., Ficoll® or PVP) and/or growth supplements (e.g., L-glutamine or hydrocortisone). Non-limiting examples of suitable growth supplements include foetal calf serum (FCS), epidermal growth factor (EGF), basic fibroblast growth factor (bFBF), fibroblast growth factor (FBF), endothelial cell growth factor (ECGF), insulin-like growth factor 1 (IGF-1) and platelet-derived growth factor (PDGF). Reducing agents may, for example, prevent the formation of disulfide bridges between free thiol groups in the cross-linking agent. Stabilising agents may, for example, be used to prevent cells from settling out of the cell culture medium. If necessary, the pH of the cell culture medium may be adjusted to a physiological pH of about 7.4 using an appropriate base. In an embodiment, sodium hydroxide (NaOH) is used as the base to neutralise or control the pH of the cell culture medium because it does not promote cell aggregation.

Harvested cells may be re-suspended at a chosen cell concentration in the polymer bio-ink or activator, or both. The concentration of cells in the polymer bio-ink and/or activator may be in the range of about $1\times10^5$ to about $5\times10^8$ cells/mL, or about $1\times10^5$ to about $1\times10^8$ cells/mL, or about $1\times10^5$ to about $1\times10^7$ cells/mL, $5\times10^5$ to about $1\times10^7$ cells/mL, or about $5\times10^5$ to about $5\times10^6$ cells/mL, or about $1\times10^6$ to about $5\times10^6$ cells/mL. In an embodiment, the cells are suspended in the polymer bio-ink and/or activator or cell culture medium at a concentration of about $4\times10^6$ cells/mL or $5\times10^6$ cells/mL of the polymer bio-ink or activator.

Any suitable cells can be used together with the polymer bio-inks and activators of the present technology. For example, suitable cells may include, but are not limited to, adherent cells such as mammalian liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblast cells, neural cells, Schwann cells, adipose cells, bone cells, bone marrow cells, cartilage cells, pericytes, mesothelial cells, cells derived from endocrine tissue, stromal cells, stem cells, progenitor cells, lymph cells, blood cells, endoderm-derived cells, ectoderm-derived cells, mesoderm-derived cells, or any combination thereof.

Other suitable cell types may include other eukaryotic cells (e.g., chinese hamster ovary), bacteria (e.g., *Helicobacter* pylon), fungi (e.g., *Penicillium chrysogenum*) and yeast (e.g., *Saccharomyces cerevisiae*).

The 3D printed hydrogel may contain at least about 100, or about 1,000, or about 5,000, or about 10,000, or about 50,000, or about 100,000, or about 150,000, or about 200,000, or about 250,000, or about 300,000, or about 350,000, or about 400,000, or about 450,000, or about 500,000 or more cells. It will be appreciated by those skilled in the art that other numbers of cells can be used.

In some embodiments the process further comprises incubating the cells suspended in the hydrogel under conditions to allow cell growth or maintenance. In some embodiments the cells may be suspended in the hydrogel under conditions that allow the differentiation of stem cells. Incubation may be at any suitable temperature and conditions. For example, incubation suitable for cell growth, maintenance or differentiation may be carried out at about 37° C. with about 5% $CO_2$ for at least 24 hours. It will be appreciated that the incubation can be carried out at any temperature and time duration that allows cell growth, maintenance or differentiation of the type of cell in the hydrogel.

In other embodiments the process further comprises incubating the cells suspended in the hydrogel under conditions that may not be suitable for cell growth. For example, incubation may be carried out under conditions that lacks oxygen, in a serum-free environment to starve the cells, in an acidic or basic environment, under an applied external pressure, in the presence of electric field, under constant shaking, or any combination thereof. Other suitable conditions for mimicking certain biological conditions will be known to those of skill in the art.

3D Bioprinting

The polymer bio-inks and activators of the present technology are suitable for drop-on-demand (DOD) bioprinting, whereby bioprinting is based on the generation of discrete droplets of the polymer bio-ink and an activator, and may include thermal inkjet, piezo inkjet and microvalve based bioprinting, among others. As with any other drop-on-demand printing technology, the polymer bio-ink and activator must be liquid inside the bioprinter cartridges. Additionally, the polymer bio-ink and activator should be made from biocompatible materials to maintain high cell viability when stored in the bioprinting cartridge.

DOD bioprinting of 3D assays comprises repetitive deposition of a droplet of the polymer bio-ink and the activator of a size and at a location on a substrate determined through the bioprinter software. Thus, in an embodiment, 3D bioprinting is carried out using a 3D bioprinter capable of forming and depositing drops. The bioprinter may have fluid reservoirs for at least the polymer bio-ink, activator and cleaning solution, a 3-axis motion control stage, a drop-on-demand droplet dispensing system, and pressure regulator to control pressure in the fluid reservoirs. The droplet dispensing system and 3-axis stage can be housed inside a sterile chamber such as a laminar flow cabinet. The printing platform may include adapters to print onto many kinds of substrates, such as micro-well plates and Petri dishes. The printing platform may be heated to about 37° C. to assist cell proliferation.

The 3D bioprinter may be controlled by a computer having software to define the printing format.

The 3D bioprinter may be configured to print (deposit) drops of polymer bio-ink and activator in a manner that allows cell integrity, viability or functionality. It will be appreciated that deposition of the polymer bio-ink and activator may be carried out in any order. A drop of polymer bio-ink can be applied to the substrate followed by a drop of activator to form the hydrogel droplet, or a drop of activator can be applied to the substrate followed by a drop of polymer bio-ink to form the hydrogel droplet.

The hydrogels formed by the process of the present technology comprise a substantially uniform 3D structure. When the hydrogel contains cells, the cells may be substantially uniformly distributed throughout the hydrogel, or they may be suspended within a part of the hydrogel of the hydrogel. The cells may be deposited in one or more selected locations in the hydrogel.

Printing substrates are biocompatible consumables used to enclose and culture the printed hydrogel structure. The substrate may be selected from any suitable vessel for containing, holding or growing cells. Examples include microtitre plate of different well configuration (6, 24, 48 and 96-well), microtitre plate with coverslip bottom of different well configuration (6, 24, 48 and 96-well), fluorodish of various sizes, chamber slides of different chamber configuration (1, 2, 4, 8 and 16), cover slip or microscope slides, or Petri dishes. In some embodiments the 3D bioprinting process is carried out to form a plurality of 3D tissue culture models on the substrate. For example, a 96-well microtitre plate is a suitable substrate and can be used for multiple cell assays. Other suitable vessels will be known to those skilled in the art.

The 3D structure of the assay may be designed using the bioprinter software. Suitable bioprinters and bioprinter software will be known to those skilled in the art. For example, for bioprinting in a 96-well plate, the bioprinter software may be configured for repetitive deposition of the droplets in the wells in layers of a chosen diameter.

The polymer bio-ink and activator react rapidly upon printing to form a hydrogel, allowing for rapid, high-throughput production of 3D structures and assays. In an embodiment, the polymer bio-ink and activator of the present technology form a hydrogel within seconds of mixing (i.e., upon printing). For example, the hydrogel may form within 5 seconds of mixing, preferably within 4, 3, 2, or 1 seconds of mixing.

The polymer bio-inks and activators of the present technology may be used with any suitable DOD bioprinting system. The present inventors recently developed a DOD bioprinting system specifically designed for the bioprinting of 3D in vitro assays. More specifically, the bioprinter is able to print polymer bio-inks and activators at up to 200 cP and with cells at up to 500 million cell/mL with greater than 95% cell viability. The developed system has been successfully used to bioprint 3D spheroid assays in a high-throughput manner. Thus, the bio-inks of the present technology are particularly useful of 3D cell printing using the 3D bioprinting system developed by the present inventors.

The fast gelling characteristic of the hydrogels of the present technology, combined with the novel printing logic of the developed bioprinter, have made the bioprinter capable of rapid printing of complex 3D assays in a 96-well format. For example, bioprinting of a 3D assay in a 96-well plate may be achieved in less than about 1 hour, preferably less than about 30 minutes, e.g., about 25 minutes, or about 20 minutes, or about 15 minutes, or less.

The polymer bio-ink and activator may be loaded into separate sterilised cartridges immediately prior to printing, or they may be stored in the cartridges. If cell bio-inks are stored in the cartridges, the cartridges should preferably be stored at 4° C. until required for further use. The polymer bio-inks and activators of the present technology may support cell viability for a prolonged period prior to printing. For example, cells may remain viable in the polymer bio-ink and activator prior to printing for at least about 2 hours. In some embodiments the polymer bio-inks and activators of the present technology can be stored at −20° C. for at least 6 months without substantially affecting cell viability. Similarly, the 3D printed hydrogels of the present technology may support cell viability for a prolonged period after printing. For example, cells may remain viable in the 3D printed hydrogel for at least about 21 days.

When ready to use, the cartridges may be connected to a clean bioprinter. Cleaning of the cartridges and/or the bioprinters (including the fluid lines, valves and nozzles) may be achieved by any suitable method known in the art, for example, by ethanol (70 v/v % in water) wiping, air drying and placing inside a biosafety cabinet. Preferably, the bioprinter is purged with the tissue culture medium being used following cleaning and prior to printing.

Applications

The 3D printed hydrogels of the present technology may have various in vitro applications. In one example, the 3D printed hydrogels of the present technology may be used to prepare assays for examination of biological phenotypes, including but not limited to, cell motility, cell migration, cell invasion, transendothelial migration, epithelial-mesenchymal transition, mesenchymal-epithelial transition, spheroid formation and growth, cell differentiation (e.g., stem cell differentiation, monitoring of cell differentiation markers), cell death (e.g., cell apoptosis; cell necrosis), cell autophagy, cell proliferation, cell metabolism, protein turnover, protein distribution and location, cell signalling and downstream events, drug efficacy, drug pharmacodynamics, drug mechanism of action, drug receptor-mediated transport, mechanisms of drug internalization, biomarker evaluation, cell-cell junctions, cell-cell signalling and downstream events, cell morphology, cell adhesion, gene expression, protein expression, cell homing, cell cycle regulation and control, cytokine release, insulin production, protein secretion and intracellular trafficking and transport, receptor-ligand binding, antibody binding, antibody specificity, protein phosphorylation, proteosomal function, enzyme function (e.g., enzyme inhibition), immunomodulation, clonogenicity, oxidative stress, protein folding, cell cytoskeleton, organelle morphology and function (e.g., mitochondria, chloroplast, peroxisomes, secretory vesicles, vacuole, ribosomes, nuclei, lysosomes, cilia, endoplasmic reticulum, golgi), membrane transport, hypoxia, angiogenesis, wound healing, neurite (outgrowth or formation), kinase function, phosphatase function, lamellipodial formation and dynamics, focal contact/adhesion formation, dynamics and signalling, cell sensing, and mechanotransduction.

The 3D printed hydrogels of the present technology may also be suitable for in vivo applications (e.g., animal studies). For example, the 3D printed hydrogels of the present technology may be used in orthotopic and subcutaneous models, with or without cells.

EXAMPLES

The following examples are illustrative of the present technology and of the beneficial effects which can be achieved with the 3D printed hydrogels of the present technology and should not be construed as limiting.

Materials 4-arm PEG-maleimide (PEG-Mal, MW 5, 10 and 20 kDa, JenKem), PEG-bis-thiol (MW 1 kDa, Sigma Aldrich), gelatin (from bovine, fish or porcine, Sigma Aldrich), 1-ethyl-3-(3-dimethylaminopropyl)carbodiimide (EDC, Sigma Aldrich), N-hydroxysulfosuccinimide (Sulfo-NHS, Sigma Aldrich), sodium hydroxide (NaOH), CRGDS, CIKVAV, CYIGSR, GCRDGPQGIWGQDRCG, GCRDPLGLDRCG and GCIPVSLRSGCG (>90%, Genscript) phosphate buffered solution without calcium chloride (PBS, Gibco), Dulbecco's modified eagle medium (DMEM, Gibco), calcium free DMEM (Gibco), sodium pyruvate (Gibco), L-glutamine (Gibco), trypsin (Sigma Aldrich), 0.22 µm syringe filter (polyethersulfone membrane, Merck Millipore), T75 and T150 flask (Corning), 15 mL centrifuge tube (Corning), ethanol (Sigma Aldrich) were used as received.

Example 1—Preparation of PEG-Mal Polymer Bio-Inks

Example 1a—Preparation of Polymer Bio-Inks in PBS

Three types of PEG-Mal polymer bio-inks were prepared in PBS buffer.

PEG-Mal Polymer Bio-Ink

PEG-Mal polymer bio-ink was prepared by mixing PEG-Mal (at 7.5 wt %) in PBS buffer solution at room temperature. After complete dissolution, the solution was filtered through a 0.22 µm syringe filter aseptically.

PEG-RGD Polymer Bio-Ink

RGD-containing PEG-Mal (PEG-RGD) polymer bio-ink was prepared by mixing CRGDS with PEG-Mal (at 10 wt %) in PBS buffer solution at room temperature for 30 minutes to yield a total of 5 mM RGD concentration. The completion of the reaction was confirmed via Ellman's assay when no free thiol was recorded. The reaction product contained PEG-RGD at 10 wt % and 5 mM RGD concentration, dissolved in PBS. After complete dissolution, an equimolar concentration of NaOH to the RGD concentration was added to the solution to bring the pH of the solution up to 7.4. The solution was sterilised via filtration through a 0.22 µm syringe filter aseptically.

PEG-Tripeptide Polymer Bio-Ink

PEG-Mal containing RGD, IKVAV and YIGSR (PEG-Tripeptide) polymer bio-ink was prepared by mixing CRGDS, CIKVAV and CYIGSR (at the desired molar concentration) with PEG-Mal (at 15 wt %) in PBS buffer solution at room temperature for 30 minutes to yield PEG-Tripeptide at 15 wt % and 0.67 mM of RGD, YIGSR and IKVAV. After complete dissolution, the pH of the solution was raised to 7.4 by dropwise addition of 1 M NaOH. The resulting solution was then sterilised by filtering it through a 0.22 µm syringe filter aseptically.

Figure 2:
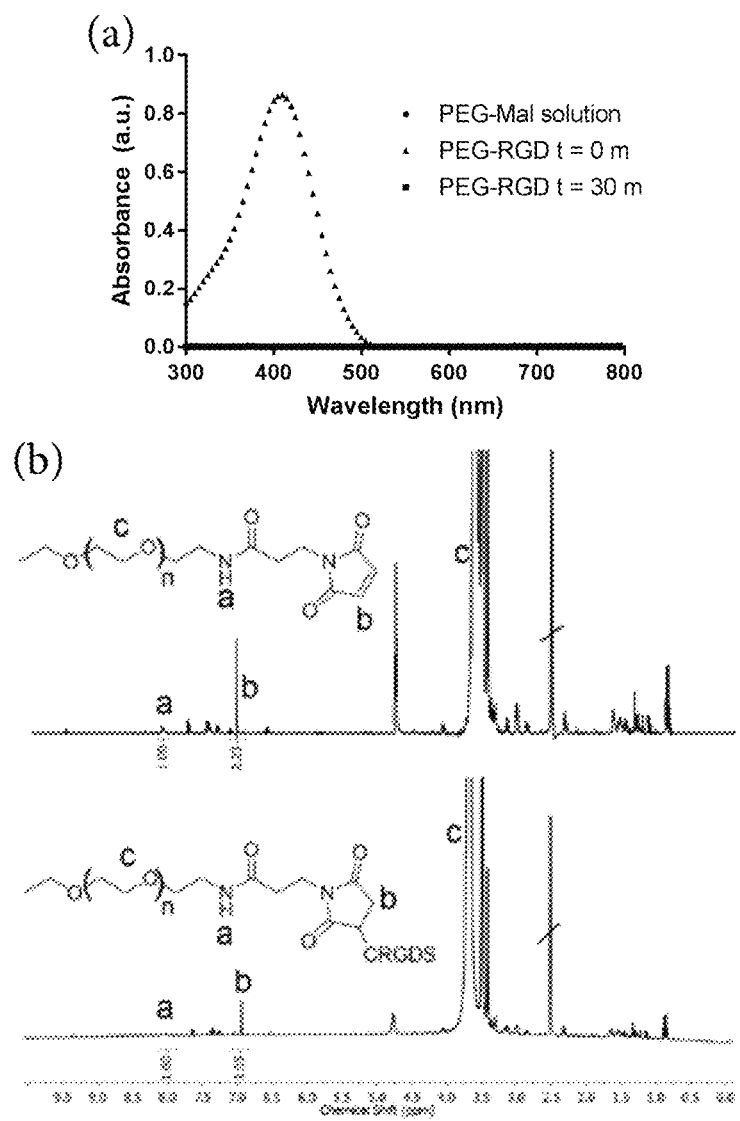
FIG. 2 shows (a) UV analysis; and (b) quantification of the CRGDS conjugation analyses by $^1$H NMR of the modification of 4-arm PEG-Mal with CRGDS.

FIG. 2 shows analyses of the modification of the 4-arm PEG-Mal with CRGDS. UV analysis showed a distinct peak at 412 nm at the start of the reaction (FIG. 2(a)). This represents the presence of $TNB^2$ (2-nitro-5-thiobenzoate) ion that is produced when the disulphide bond of the Ellman's reagent was cleaved by a thiol moiety (in this case the CRGDS) and ionised. In contrast, such peak was absent on the 4-arm PEG-Mal solution without CRGDS and after the reaction was allowed to proceed for 30 minutes, indicating that the 4-arm PEG-Mal is not reacting with the Ellman's reagent and the CRGDS was completely reacted after 30 min, respectively. Quantification of the CRGDS conjugation was confirmed using $^1$H NMR, by comparing the amide and the maleimide proton peak (FIG. 2(b)).

Example 1b—Preparation of Polymer Bio-Ink in Cell Culture Medium

RGD-containing PEG-Mal polymer bio-ink in cell culture medium was prepared following the procedure in Example 1a using an appropriate cell-culture solution for the cells to be printed instead of a PBS solution. The resulting polymer bio-ink was sterilised via filtration (0.22 µm filter) aseptically.

Polymer bio-inks prepared according to Example 1 were stored at −20° C. until required for further use. The polymer bio-inks may be stored at −20° C. for at least 6 months without affecting functionality.

Example 2—Preparation of PEG-Bis-Thiol and GCIPVSLRSGCG Activator

Example 2a—Preparation of Activators in PBS

Activator was prepared by mixing dithiothreitol (DTT), PEG-bis-thiol, GCIPVSLRSGCG and GCRDPLGLDRCG, or various combinations thereof, in PBS at a total thiol concentration equimolar to the maleimide concentration of the complementing polymer bio-ink. The resulting solutions were sterilised via filtration through a 0.22 µm syringe filter aseptically.

Example 2b—Preparation of Activators in Cell Culture Medium

Activator was prepared by mixing a dithiothreitol (DTT), PEG-bis-thiol, GCIPVSLRSGCG and GCRDPLGLDRCG in an appropriate cell-culture solution for the cells to be printed, at a total thiol concentration equimolar to the maleimide concentration of the complementing bio-ink. The resulting solution was sterilised via filtration (0.22 µm filter) aseptically.

Activators prepared according to Example 2 were stored at −20° C. until required for further use. The activators may be stored at −20° C. for at least 6 months without affecting functionality.

Example 3—Cell Culture

SK-N-BE(2) (human neuroblastoma), $Kras^{G12D}$ and $p53R^{172H}$ (pancreatic ductal adenocarcinoma), MCF7 (human breast cancer) and U87vIII (human glioblastoma) cells were individually maintained in 10% foetal calf serum (FCS)/DMEM at 37° C./5% $CO_2$. Human non-small cell lung cancer H460 cells were cultured in Roswell Park Memorial Institute (RPMI) 1640 media and 10% FCS at 37° C./5% $CO_2$. Cell lines were routinely screened and free of mycoplasma contamination.

Example 4—Trypan Blue Exclusion

SK-N-BE(2), $Kras^{G12D}$ and $p53R^{172H}$, H460 and U87vIII cells cultured according to Example 3 were harvested from T75 flasks using trypsin/PBS and pelleted using centrifugation. Cells were re-suspended in a polymer bio-ink containing PEG-Mal and PEG-RGD at 10 wt % and 5 mM RGD concentration to a cell concentration of $2\times10^6$ cells/mL. Samples were split into two groups: printed and a non-printed control. The printed samples were passed through the 3D bioprinter and kept in a sterile condition at room temperature for 30 minutes. Dead cells were identified using 0.4% trypan blue stain (Invitrogen). Cell counts were obtained by counting the number of live and dead cells in each sample. Percentage cell viability was determined by dividing the total number of live cells by the total number of cells (live+dead).

Example 5—Preparation of Cell Polymer Bio-Ink

Cultured cells of interest at certain confluency were harvested by following the procedure of Example 4. To make up the cell polymer bio-ink, harvested cells were re-suspended in sterilised polymer bio-ink prepared according to Example 1(a) or 1(b) at the appropriate cell concentration to give $2\times10^6$ cells/mL in 1 mL of sterilised polymer bio-ink.

Example 6—Preparation of Cell Activator

Cultured cells of interest at certain confluency were harvested by following the procedure of Example 4. To make up the cell activator, harvested cells were re-suspended in sterilised activator prepared according to Example 2(a) or 2(b) at the appropriate cell concentration.

Example 7-3D Cell Viability Assay

Live/dead staining was used to monitor the viability of the hydrogel encapsulated cells. Calcein AM (1 μL mL$^{-1}$) and ethidium homodimer-I (4 μL mL$^{-1}$) in DMEM were used to stain the live and dead cells, respectively. Cell polymer bio-ink prepared according to Example 5 was used to 3D bioprint hydrogels with encapsulated cells. After the required incubation period, the bioprinted hydrogels were incubated with the live/dead stain for at least 2 h at 37° C./5% $CO_2$, prior to confocal fluorescence microscopy analysis.

Example 8—Rheological Characterisation

Mechanical properties were studied for a hydrogel prepared from 4-arm PEG-Mal hydrogel with 5 mM RGD (10 wt %) (prepared according to Example 1(a)) and cross-linked with PEG-bis-thiol and MMP-2 responsive bis-cysteine peptide GCIPVSLRSGCG (mixed at 50:50 thiol molar concentration) (prepared according to Example 2(a)).

Hydrogel rheology was measured using an Anton-Paar modular compact rheometer (MCR) 302 equipped with the concentric cylindrical spindle and cup system. Viscosity measurement was conducted at a shear rate value of between 1-1000 s$^{-1}$. Rheological characteristics of the hydrogel were measured using the same machine equipped with a parallel-plate geometry (25 mm in diameter) system and a solvent trap to minimise liquid evaporation. Rheological measurements were conducted on a preheated plate and maintained at a constant temperature of 37° C. Amplitude strain sweep experiments (y: 1-100%) were carried out to determine the linear viscoelastic region (LVR) at a fixed frequency of 10 Hz. Once the LVR of each sample was established, dynamic frequency sweeps were performed (w: 0.1-10 Hz) at fixed strain in the linear viscoelastic region of the hydrogel. Time sweep measurements were performed typically at a fixed frequency (10 Hz) and strain amplitude (within the LVR).

Figure 3:
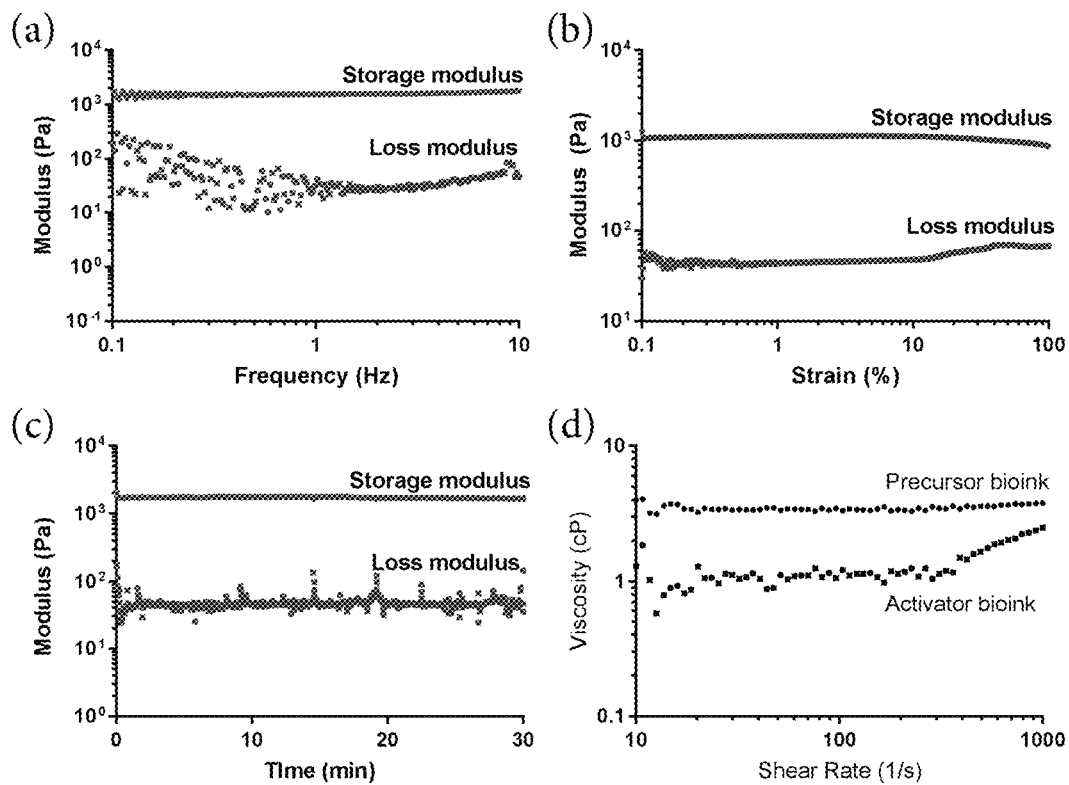
FIG. 3 shows the results of (a) frequency; (b) strain; (c) stiffness; and (d) viscosity rheological studies of a hydrogel prepared from 4-arm PEG-Mal hydrogel with 2.5 mM RGD (10 wt %) and cross-linked with PEG-bis-thiol and MMP-2 responsive bis-cysteine peptide (mixed at 50:50 thiol molar concentration).

As shown in FIG. 3, the frequency (FIG. 3(a)) and strain (FIG. 3(b)) sweep studies confirmed that the mechanical properties of the gel were independent of these two parameters.

Subsequent determination of the stiffness was conducted at constant frequency and strain values within the viscoelastic region of the hydrogel (FIG. 3(c)). Measurement was conducted within 1 minute after casting the hydrogel. FIG. 3(c) shows that the storage modulus (G') value was always higher than the loss modulus (G") value throughout the measurement period. The constant storage modulus value at around 1.1 kPa indicated that the gelation process had completed within the 1 minute period. Viscosity studies on both the polymer bio-ink and activator showed a viscosity value of less than 10 cP, making both the polymer bio-inks and activators extremely suitable for the drop-on-demand bioprinting process (FIG. 3(d)).

Figure 4:
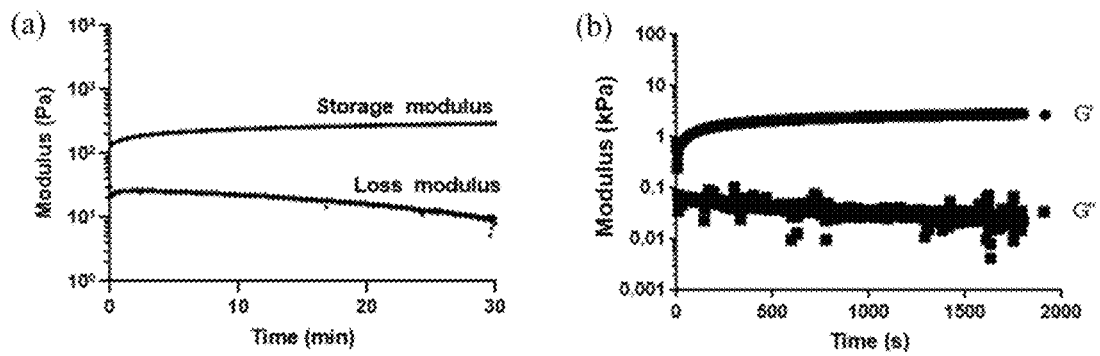
FIG. 4 shows the results of stiffness rheological studies of (a) blank 4-arm PEG-Mal hydrogel at 7.5 wt % crosslinked with PEG-bis-thiol and (b) PEG-Tripeptide hydrogel crosslinked with MMP-responsive, bis-cysteine peptide activator.

Mechanical properties were also studied for a hydrogel prepared from 4-arm PEG-Mal blank polymer bio-ink (prepared according to Example 1(a)) cross-linked with PEG-bis-thiol (prepared according to Example 2(a)) and a hydrogel prepared from PEG-Tripeptide (prepared according to Example 1(a)) cross-linked with an MMP-sensitive activator (GCIPVSLRSGCG) prepared according to Example 2(a)). Determination of the stiffness was conducted at constant frequency and strain values within the viscoelastic region of the PEG-Mal hydrogel (FIG. 4(a)) and PEG-Tripeptide hydrogel (FIG. 4(b)). Measurement was conducted within 1 minute after casting the hydrogel. FIGS. 4(a) and 4(b) show that the storage modulus (G') value was always higher than the loss modulus (G") value throughout the measurement period. This observation confirmed the presence of a hydrogel when the bio-ink and the activator were mixed. Quantitatively, the hydrogels formed from the PEG-Mal blank polymer bio-ink and PEG-bis-thiol activator had a stiffness value of around 0.2 kPa and the PEG-Tripeptide/MMP-sensitive hydrogel had a stiffness value of around 1.6 kPa.

Example 9-3D Bioprinting Platform

The components of the 3D bioprinter used in the present examples include a 3-axis motion control stage, a drop-on-demand droplet dispensing system and a pressure regulator to control pressure in the fluid reservoirs. The droplet dispensing system and 3-axis stage can be housed inside a sterile chamber such as a laminar flow cabinet. The printing platform includes adapters to print onto many kinds of substrate, such as micro-well plates and Petri dishes. The printing platform can be heated to 37° C. to assist cell proliferation.

The 3-axis motion control stage (MX80S, Parker) is capable of accurately positioning the droplet dispensing system at a resolution of 10 μm in all three (X, Y and Z) dimensions. The ten droplet dispensing systems consist of a solenoid valve (VHS Series Solenoid Valve, The Lee Company) with a jewelled orifice dispensing nozzle (MINSTAC Nozzle, The Lee Company) controlled by a microcontroller (Arduino Mega 2560, Arduino). The internal diameter of the jewelled orifice nozzle can be between 127 and 254 μm depending on the fluid viscosity and the desired droplet volume. Each droplet dispensing system is attached to a static pressure reservoir for the polymer bio-ink and activator solutions to be dispensed via flexible tubing. The desired droplet volume can also be adjusted using the backpressure in the fluid reservoir and the solenoid valve open time. Typically, the backpressure is set to a pressure between 1 and 300 kPa, the solenoid valve open time is 0.3 ms or greater and the droplet volume is between 1 and 500 nL. Flexible tubing connecting the polymer bio-ink and activator reservoirs were kept as short as possible in order to minimize the amount of time it would take to prime the system and to purge it at the end of a printing routine.

Example 10—Control Software

The 3D bioprinter was controlled via custom software developed for printing biological assays. The software includes a graphical user interface (GUI) and was written in the Python programming language. Through the GUI the end user can select different assay printing routines and change the assay parameters, such as droplet spacing and droplet volume. The user can also manually control the spatial position of the droplet dispensing system and create a custom pattern of droplets. Additional features of the software include routines for priming and purging the droplet dispensing system.

Example 11-3D bioprinting

Sterile polymer bio-ink and activator were heated to room temperature prior to printing. The cells of interest were mixed with the polymer bio-ink and/or the activator at the desired cell concentration. All solutions were then loaded into the bioprinter sample tray. Bioprinting was conducted using the Rastrum™ modular 3D bioprinter (Inventia Life Science (ILS)). The structure was designed using the Rastrum™ software (ILS). Two different bioprinted samples were printed; a cylindrical structure with a diameter of about 6.35 cm and 400 µm in thickness and a half-sphere structure with a diameter of 100 µm, sitting on top of an inert gel layer with 6.35 cm diameter and 100 µm thickness. Both polymer bio-ink and activator solutions were printed at a printing pressure of between 20 and 100 kPa. Prior to the bioprinting process, the Rastrum™ bioprinter conducted automated sterilisation and priming steps.

The generation of the 3D object was achieved by the deposition of a polymer bio-ink droplet, which was then immediately followed by the deposition of an activator droplet on top of it, at the determined location by the software. All printing was conducted in a 96-well plate (Corning). Upon completion, relevant cell culture media for the cells (150 µL) was added and the plate was transferred into an incubator.

FIG. 1 is a representative schematic of the 3D bioprinting process. The polymer bio-ink used comprised 4-arm PEG-maleimide (PEG-Mal), CRGDS and the desired cancer cells (prepared according to Examples 1(a) and 5). The activator comprised a mixture of PEG-bis-thiol and bis-thiol MMP responsive peptide GCIPVSLRSGCG (prepared according to Example 2(a)). Both solutions were loaded into the ILS 3D bioprinter system according to Example 9, which deposited the combination of the polymer bio-ink and activator in a spatially controlled manner. Gelation occurred instantaneously upon mixing of both solutions, producing three-dimensionally encapsulated cells inside the hydrogel, within a 96-well plate.

Example 12-3D Bioprinting of Pancreatic Ductal Adenocarcinoma Cells ($Kras^{G12D}$ and $p53^{R172H}$)

Multiple samples of three-dimensionally encapsulated cancer cells inside thiol-maleimide cross-linked PEG hydrogel were bioprinted using the ILS 3D bioprinter. Specifically, simultaneous delivery of cancer cells, polymer bio-ink and activator were done using the bioprinter to achieve rapid creation of in situ cell encapsulation inside the bioprinted hydrogel.

Cell Culture

Pancreatic ductal adenocarcinoma cells $Kras^{G12D}$ and $p53^{R172H}$ at 80% confluency in a T150 flask were washed with 3 mL PBS. Following aspiration of excess PBS, 3 mL of trypsin was added and the flask was incubated at 37° C. to dissociate cells from flask surface for 5 minutes. Subsequently, 7 mL of tissue culture media prepared by mixing DMEM with FCS at 10 v/v % was added and the dissociated cells were transferred into a 15 mL tube. The cell dispersion was centrifuged at 400 g for 3 minutes. The supernatant was discarded and the cell pellet was re-suspended in 5 mL of media. Cell counting was then conducted by mixing equal volumes of cell suspension and trypan blue stain to determine the cell concentration.

Substrate 96-well plate supplied by Corning incorporated was used as received. The sterile packaging was opened in a sterile environment to maintain the content sterility.

Polymer Bio-Ink

To prepare the polymer bio-ink, PEG-Mal (0.150 g) was dissolved in 1.5 mL PBS to yield a 10 wt % polymer bio-ink. If PEG-RGD was to be incorporated, CRGDS (1.34 mg) was added into the solution and stirred for 30 minutes to yield 10 wt % PEG-Mal/PEG-RGD polymer bio-ink with 5 mM RGD. Into the solution, 2.5 µL of 1M NaOH was added to raise the pH of the solution to 7.4. The solution was then filtered through a 0.22 µm syringe filter under a sterile environment.

Harvested $Kras^{G12D}$ and $p53^{R172H}$ dispersed in 1 mL DMEM at $2 \times 10^6$ cells/mL was centrifuged to give a cell pellet of 500,000 cells. The resulting pellet was then re-dispersed in the polymer bio-ink (1 mL) to give a cell polymer bio-ink solution with dispersed $Kras^{G12D}$ and $p53^{R172H}$ cells at $2 \times 10^6$ cells/mL.

Activators

Two different activators were prepared in order to produce both non-MMP and MMP responsive hydrogels. The two activators were prepared from either PEG-bis-thiol (0.01975 g) alone, or a combination of PEG-bis-thiol (0.0096 g) and GCIPVSLRSGCG (0.0111 g), each dissolved in 1 mL PBS to yield an activator with an equimolar thiol concentration to the maleimide in the bio-ink. Each solution was then filtered through a 0.22 µm syringe filter under a sterile environment.

Cell Printing Conditions

Cell polymer bio-ink and activator were loaded into the relevant cartridges, connected to the bioprinter. Both cell polymer bio-ink and activator were connected to a 0.007" nozzle, operating at 10 Psi.

The printer was initially cleaned via ethanol (70 v/v % in water) wiping and air dried. The fluid lines, valves and nozzles were also sterilised via ethanol, water and tissue culture media purging, in that order. The cell polymer bio-ink and activator were then loaded into their respective vials. The printhead was then primed prior to starting the printing routine.

The 3D structure of the assay was designed using ILS custom-made software. The 3D assay was comprised of 3-layers of circular shape gel, with a total diameter of 6.35 mm. Bioprinting of the 3D assays was conducted by repetitive deposition of a droplet of a polymer bio-ink and activator pair at the determined location through the software.

Cell Concentrations

Cell polymer bio-ink with a concentration of $2 \times 10^6$ cells/mL was used in this experiment.

Cell Viability

Cell viability of greater than or equal to 95% was obtained.

Example 13-3D Bioprinting of Human Breast Cancer Cells (MCF7)

Cell Culture

MCF7 cells at 80% confluency in a T75 flask were washed with 3 mL PBS. Following aspiration of excess PBS, 1 mL of trypsin was added and the flask was incubated at 37° C. to dissociate cells from flask surface for 3 minutes. Subsequently, 7 mL of tissue culture media prepared by mixing DMEM with FCS at 10 v/v % was added and the dissociated cells were transferred into a 15 mL tube. The cell dispersion was centrifuged at 400 g for 3 minutes. The supernatant was discarded and the cell pellet was re-suspended in 5 mL of media. Cell counting was then conducted by mixing equal volumes of cell suspension and trypan blue stain to determine the cell concentration.

Substrate 96-well plate supplied by Corning incorporated was used as received. The sterile packaging was opened in a sterile environment to maintain the content sterility.

Polymer Bio-Ink

To prepare the blank polymer bio-ink, PEG-Mal (0.1125 g) was dissolved in 1.5 mL PBS to yield a 7.5 wt % polymer bio-ink. PEG-Tripeptide was prepared by mixing CRGDS (0.54 mg), CIKVAV (0.64 mg), CYIGSR (0.70 mg) and PEG-Mal (0.225 g) in 1.5 mL of PBS for 30 minutes to yield 15 wt % PEG-Tripeptide with 0.67 mM of RGD, IKVAV and YIGSR each. The pH of the solution was raised to 7.4 by the dropwise addition of 1M NaOH. Both solutions were filtered through a 0.22 µm syringe filter aseptically.

Activators

Two different activators were prepared in order to produce both non-MMP and MMP responsive hydrogels. The two activators were prepared from either PEG-bis-thiol (0.015 g) or GCRDPLGLDRCG (0.019 g), each dissolved in 1 mL PBS to yield an activator with an equimolar thiol concentration to the maleimide in the blank bio-ink and PEG-Tripeptide, respectively. Subsequently, the MMP-responsive activator solution was adjusted to pH 7.4 via dropwise addition of 1M NaOH. Each solution was then filtered through a 0.22 µm syringe filter aseptically.

Harvested MCF7 dispersed in 1 mL DMEM was centrifuged to give a cell pellet of 10.000,000 cells. The resulting pellet was then re-dispersed in the activator (1 mL) to give a cell MMP-activator solution with dispersed MCF7 cells at $1\times10^7$ cells/mL.

Cell Printing Conditions

The polymer bio-inks, PEG-bis-thiol activator and MMP-responsive cell activator were loaded into the relevant cartridges, connected to the bioprinter. The polymer bio-inks, PEG-bis-thiol activator and MMP-responsive cell activator were each connected to a 0.007" nozzle, operating in between 25 and 30 kPa.

The printer was initially cleaned via ethanol (70 v/v % in water) wiping and air dried. The fluid lines, valves and nozzles were also sterilised via ethanol and sterile water purging, in that order. The polymer bio-inks, PEG-bis-thiol activator and MMP-responsive cell activator were then loaded into their respective vials. The printhead was then primed prior to starting the printing routine.

The 3D structure of the assay was designed using ILS custom-made software. The 3D assay was comprised of a bottom gel layer with a diameter of 6.35 cm and 100 µm thickness and a cell-laden, dome-shaped gel with a diameter of 1 mm and 200 µm thickness.

Cell Concentrations

Cell activator with a concentration of $1\times10^7$ cells/mL was used in this experiment.

Cell Viability

Cell viability of greater than or equal to 95% was obtained.

Example 14—Comparison of Cellular Arrangement

The effect of the hydrogel micro-environment on the cellular arrangement of pancreatic cancer was tested using the polymer bio-ink and activator of the present technology. Pancreatic cancer cells were chosen because their biological characteristics are highly dependent on the cell culture environment. Two different cellular arrangements were tested by bioprinting a hydrogel sample with a diameter of 6 mm and height of 0.4 mm on a 96-well plate. First, cells were 3D bioprinted on top of the hydrogel and second, cells were printed inside (i.e., encapsulated in) the hydrogel. In both cellular arrangements tested, viable cells were observed. Moreover, cell-gel interactions were visible, as represented by the ability of the cells to form protrusions into the hydrogel. Overall, biocompatible and bio relevant 3D assays were successfully bioprinted with the PEG-based polymer bio-inks.

Pancreatic Cancer Cells Seeded on Top of the Hydrogel

A cell polymer bio-ink was prepared from harvested pancreatic ductal adenocarcinoma cells (Kras$^{G12D}$ and p53$^{R172H}$) and a 4-arm PEG-Mal (10 kDa), with 5 mM RGD polymer bio-ink for 3D bioprinting. Pancreatic cancer cells were dispersed in the cell polymer bio-ink at a concentration appropriate to seed an estimated 5,000 cell/well.

A cell free hydrogel was initially 3D bioprinted from 4-arm PEG-Mal (10 kDa), with 5 mM RGD polymer bio-ink and PEG-bis-thiol and MMP-2 (GCIPVSLRSGCG) activator (at 50:50 thiol concentration ratio) on a 96-well plate. The cell polymer bio-ink was then printed together with the PEG-bis-thiol and MMP-2 activator (at 50:50 thiol concentration ratio) on top of the hydrogel to seed an estimated 5,000 cell/well.

Microscopy images were taken of the pancreatic cancer cells seeded on top of the hydrogel. After 3 days incubation morphological differences of the same cells when seeded on top of a tissue culture plastic were observed. When seeded on top of the hydrogel, both cell-gel and cell-cell interactions were promoted that led to the formation of expanded cell network with extensive cell protrusions in all three dimensions. After 3 days incubation, cultured cells were confirmed to be viable via a live/dead staining assay. Cell viability was confirmed to be >98%, with small individual dead cells clearly visible within the larger living cell cluster.

The pancreatic cancer cells were also seeded on various substrates for comparison. Microscopic images showed that pancreatic cancer cells seeded on top of a tissue culture well-plate were very individualistic. In contrast, pancreatic cancer cells formed an expanded network between multiple cells when seeded on top of the hydrogel. While seeded on top of a hydrogel, the cells were able to invade into the hydrogel and formed a 3D cellular network. Microscope scanning into the gel on the z-axis confirming the presence of a 3D cellular network within the hydrogel.

Pancreatic Cancer Cells Encapsulated in the Biologically Inert Hydrogel

Pancreatic ductal adenocarcinoma cells (KrasG$^{12}$D and p53$^{R172H}$) were dispersed in the polymer bio-ink with no PEG-RGD at 2×10⁶ cells/mL to yield the cell polymer bio-ink and the cell polymer bio-ink printed together with the activator with no MMP-2 responsive peptide. In situ encapsulation was achieved by directly 3D bioprinting the cell-bio-ink with the PEG-bis-thiol activator on the 96-well plate.

Confocal images showed pancreatic cancer cells encapsulated inside the hydrogel. Morphology of the cells was confirmed over the incubation period. Due to the lack of RGD and MMP-2 cross-linker, cells were rounded in morphology inside the gel. This morphology indicated that the cells were unable to interact with the hydrogel to generate focal adhesion, and were unable to move inside the gel. Live/dead assay was conducted on the encapsulated cells after 3 days incubation period. Fluorescence images showed viable cells (>95% viability) after 3 days of incubation.

Pancreatic Cancer Cells Encapsulated in the Biologically Active Hydrogel

Pancreatic ductal adenocarcinoma cells ($Kras^{G12D}$ and $p53^{R12H}$) were dispersed in the cell polymer bio-ink at 2×10⁶ cells/mL and printed together with the MMP-2 responsive peptide activator (at 50:50 thiol concentration ratio). In situ encapsulation was achieved by directly 3D bioprinting the cell polymer bio-ink with the PEG-bis-thiol and MMP-2 activator on the 96-well plate. The MMP-2 activator was used to allow cellular invasion.

Confocal images showed pancreatic cancer cells encapsulated inside the hydrogel. Morphological changes of the cells were confirmed over the incubation period. Inside the gel, cell-cell interactions were represented by the formation of cell clusters, while cell-gel interactions and cell invasion were confirmed by the presence of cellular membrane protrusion. Live/dead assay was conducted on the encapsulated cells after 3 and 6 days incubation period. Bright field and fluorescence mages showed viable cells (>98% viability) after 3 days of incubation and confirmed the presence of cell-cell and cell-gel interactions. Cellular invasion was more pronounced at 6 days incubation, indicating strong cell-gel interactions. At the same time, cellular viability of >98% was also maintained after 6 days incubation inside the gel.

MCF7 Breast Cancer Cells Seeded in the Hydrogel

Cellular activities were confirmed via observation of cell morphologies under a bright-field microscope after 3-day incubation. Aggregation of single MCF7 cells were visible after the incubation period, forming multiple spheroids in the pre-defined gel area, indicating the ability of individual MCF7 cells to move to each other inside the hydrogel.

Example 15—Modification of Gelatin from Cold Fish Skin with Maleimide Group

Gelatin from fish skin (1 g) was dissolved in 20 mL of 2-(N-morpholino)ethanesulfonic acid (MES) buffer at 40° C. In a separate container, 6-maleimidohexanoic acid (MHA; 0.211 g), 1-ethyl-3-(3-dimethylaminopropyl) carbodiimide (EDC, at 1:20 EDC:MHA molar ratio) and N-hydroxysuccinimide (NHS, at 1:2 NHS:EDC molar ratio) were dissolved in 1 mL MES buffer and left to stir for 20 minutes to activate the carboxylic acid (COOH) groups. The solution of activated COOH group was then transferred into the gelatin solution and the reaction was left to proceed for 24 h. The resulting solution was purified via dialysis against 10 mM hydrochloric acid (HCl) and 1 wt % sodium chloride (NaCl) for 2 days, followed by dialysis against 10 mM HCl for 1 day. The purified gelatin solution was then freeze dried to yield maleimide modified fish gelatin.

Example 16—Modification of Gelatin from Porcine Skin with Maleimide Group

Gelatin from porcine skin (gel strength 300, type A, 1 g) was dissolved in 20 mL of MES buffer at 40° C. In a separate container, MHA (0.139 g), EDC (at 1:20 EDC:MHA molar ratio) and N-hydroxysuccinimide (NHS, at 1:2 NHS:EDC molar ratio) were dissolved in 1 mL MES buffer and left stirred for 20 minutes to activate the COOH groups. The solution of activated COOH group was then transferred into the gelatin solution and the reaction was left to proceed for 24 h. The resulting solution was purified via dialysis against 10 mM HCl and 1 wt % NaCl for 2 days, followed by dialysis against 10 mM HCl for 1 day. The purified gelatin solution was then freeze dried to yield maleimide modified porcine gelatin.

Example 17—Gelation of Maleimide Modified Gelatin

Maleimide modified gelatin from both porcine and cold fish skin, synthesised in Examples 15 and 16, were each dissolved in PBS at 20 wt % to yield the polymer bio-inks. The pH of each solution was neutralised to pH 7.4 with 1M NaOH. To prepare the activator, PEG-bis-thiol at equal SH molar concentration to the maleimide molar concentration was dissolved in PBS. Gelation was achieved by mixing equal volumes of each polymer bio-ink and activator.

Example 18-3D Bioprinting of Collagen-Containing PEG Hydrogel

Substrate

A cell culture dish supplied by Thermofisher was etched with a target grid mimicking the dimension of a 96-well plate.

Polymer Bio-Ink

To prepare polymer bio-ink, PEG-Mal (0.15 g) was dissolved in 1.5 mL PBS to yield a 10 wt % polymer bio-ink. The solution was filtered through a 0.22 μm syringe filter aseptically.

Activators

Collagen containing activator was prepared by mixing GCRDPLGLDRCG (0.01 g) in 0.5 mL PBS. Subsequently, 0.5 mL of Type I bovine collagen (3.1 mg) was mixed into the activator solution to yield a collagen containing MMP-activator. Subsequently, the pH of the solution was adjusted to pH 7.4 via dropwise addition of 1M NaOH. The solution was then filtered through a 0.22 μm syringe filter aseptically.

Printing Conditions

Polymer bio-ink and collagen containing MMP-activator were loaded into the relevant cartridges, connected to the bioprinter. Both polymer bio-ink and activator were connected to a 0.007" nozzle, operating in between 25 and 30 kPa.

The 3D structure of the assay was designed using ILS custom-made software. The 3D rectangular prism structure was comprised of a bottom gel layer with a length and width of approximately 4.5 cm and 150 μm in thickness.

Structure VALIDATION

The resulting hydrogel structures were imaged using a USB digital microscope.

Example 19—Fibroblast Culture Inside the Collagen-Containing PEG Hydrogel

The polymer bio-ink with collagen was prepared by mixing Type I bovine collagen with 10 wt % PEG-Mal in PBS at 1:1 v/v ratio. The pH of the solution was raised to 7.4 through the dropwise addition of 1M NaOH solution. PEG-bis-thiol activator containing equimolar thiol to maleimide concentration was prepared in PBS. Harvested human lung fibroblast (MRC-5) cells were pelleted and re-suspended in the collagen-containing polymer bio-ink. PEG hydrogel was prepared by firstly transferring the polymer bio-ink into a well plate and followed by transferring an equal volume of the cell-containing activator into the same well. 100 μL of DMEM+10 v/v % FBS was then added into each well and the samples was incubated for 6 days, with a bright field images taken at day 0, 3 and 6 to monitor cell activities.

Biological compatibility of the gel for fibroblast culture was assessed by looking at the change in fibroblast morphology from rounded morphology into spindle like morphology.

Those skilled in the art will appreciate that the present disclosure is susceptible to variations and modifications other than those specifically described. It is to be understood that the invention includes all such variations and modifications without departing from the spirit or scope of the invention as broadly described. The present embodiments are, therefore, to be considered in all respects as illustrative and not restrictive.

The present disclosure also includes all of the steps, features, compositions and compounds referred to or indicated in this specification, individually or collectively, and any and all combinations of any two or more of said steps, features, compositions and compounds.

REFERENCES

1. Caliari, S. R.; Burdick, J. A., A practical guide to hydrogels for cell culture. Nature Methods 13, 405 (2016).
2. Murphy, S. V.; Atala, A., 3D bioprinting of tissues and organs. Nature Biotechnology 32, 773 (2014).
3. Donderwinkel, I.; van Hest, J. C. M.; Cameron, N. R., Bio-inks for 3D bioprinting: recent advances and future prospects. Polymer Chemistry 8, 4451-4471 (2017).
4. Jungst, T.; Smolan, W.; Schacht, K.; Scheibel, T.; Groll, J., Strategies and Molecular Design Criteria for 3D Printable Hydrogels. Chemical Reviews 116, 1496-1539 (2016).
5. Lowe, S. B.; Tan, V. T. G.; Soeriyadi, A. H.; Davis, T. P.; Gooding, J. J., Synthesis and High-Throughput Processing of Polymeric Hydrogels for 3D Cell Culture. Bioconjugate Chemistry 25, 1581-1601 (2014).
6. Gao, G.; Hubbell, K.; Schilling, A. F.; Dai, G.; Cui, X., Bioprinting Cartilage Tissue from Mesenchymal Stem Cells and PEG Hydrogel. In *3D Cell Culture: Methods and Protocols*, Koledova, Z., Ed. Springer New York: New York, NY, 2017; pp 391-398.
7. Gao, G.; Yonezawa, T.; Hubbell, K.; Dai, G.; Cui, X., Inkjet-bioprinted acrylated peptides and PEG hydrogel with human mesenchymal stem cells promote robust bone and cartilage formation with minimal printhead clogging. Biotechnology Journal 10, 1568-1577 (2015).

The invention claimed is:

1. A drop on demand 3D printed hydrogel formed from a maleimide containing polymer selected from a poly(ethylene glycol) (PEG) maleimide, a gelatin maleimide, or a combination thereof, cross-linked using a bis-thiol containing cross-linking agent having at least two thiol functional groups, wherein the hydrogel is formed within 1 second or less from printing of the maleimide containing polymer and the cross-linking agent, with NaOH or other suitable base to adjust pH of the polymer or cross-linking agent.

2. The 3D printed hydrogel according to claim 1, wherein the maleimide containing polymer comprises a PEG maleimide.

3. The 3D printed hydrogel according to claim 2, wherein the maleimide containing polymer is PEG-maleimide substituted with at least one bioactive molecule selected from RGD, YIGSR and IKVAV.

4. The 3D printed hydrogel according to claim 1, wherein the maleimide containing polymer comprises a gelatin maleimide.

5. The 3D printed hydrogel according to claim 4, wherein the maleimide containing polymer is gelatin maleimide and the bis-thiol containing cross-linking agent is PEG-bis-thiol.

6. The 3D printed hydrogel according to claim 1, wherein the bis-thiol containing cross-linking agent is selected from the group consisting of synthetic polymers, biopolymers, small molecules, bioactive molecules, and any combination thereof.

7. The 3D printed hydrogel according to claim 1, wherein the bis-thiol containing cross-linking agent is selected from PEG-bis-thiol, matrix metalloproteinase (MMP) responsive peptides, or a combination thereof.

8. The 3D printed hydrogel according to claim 7, wherein the bis-thiol containing cross-linking agent is a PEG-bis-thiol.

9. The 3D printed hydrogel according to claim 7, wherein the bis-thiol containing cross-linking agent is a matrix metalloproteinase (MMP) responsive peptide.

10. The 3D printed hydrogel according to claim 9, wherein the MMP-responsive peptide is an MMP-responsive bis-cysteine peptide.

11. The 3D printed hydrogel according to claim 10, wherein the MMP-responsive peptide is selected from the group consisting of GCIPVSLRSGCG (SEQ ID NO: 1), GCRDGPQGIWGQDRCG (SEQ ID NO: 2), GCRDPLGLDRCG (SEQ ID NO: 3), GCRDEAPLKQDRCG (SEQ ID NO: 4), and any combination thereof.

12. The 3D printed hydrogel according to claim 11, wherein the MMP-responsive peptide is GCIPVSLRSGCG (SEQ ID NO: 1), GCRDPLGLDRCG (SEQ ID NO: 3), or a combination thereof.

13. The 3D printed hydrogel according to claim 1, wherein the molar ratio of maleimide containing polymer to bis-thiol containing cross-linking agent is in the range of 10:1 to 1:10.

14. The 3D printed hydrogel according to claim 1, containing cells.

15. The 3D printed hydrogel according to claim 14, wherein the cells are suspended within a part of the hydrogel or the cells are substantially uniformly suspended throughout the hydrogel.

16. The 3D printed hydrogel according to claim 15, wherein the concentration of printed cells is in the range of $1 \times 10^5$ to $5 \times 10^8$ cells/mL.

17. The 3D printed hydrogel according to claim 1, wherein the cells are selected from the group consisting of liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblast, neural cells, Schwann cells, adipose cells, bone cells, bone marrow cells, cartilage cells, pericytes, mesothelial cells, cells derived from endocrine tissue, stromal cells, stem cells, progenitor cells, lymph cells, blood cells, endoderm-derived cells, ectoderm-derived cells, and mesoderm-derived cells, and any combination thereof.

18. The 3D printed hydrogel according to claim 1, further comprising a bioactive molecule.

19. The 3D printed hydrogel according to claim 18, wherein the bioactive molecule is: (i) a free bioactive molecule, (ii) bound to the maleimide containing polymer, (iii) bound to the bis-thiol containing cross-linking agent, or (iv) bound to both the maleimide containing polymer and the bis-thiol containing cross-linking agent.

20. The 3D printed hydrogel according to claim 19, wherein the bioactive molecule is selected from the group consisting of a peptide, MMP-responsive peptide, protein, polysaccharide, drug, therapeutic agent, antibody, small molecule inhibitor, kinase inhibitor, phosphatase inhibitor, antigen, pathogen, platelet, growth factor, cytokine, amino acid, nutrient, conditioned media, antibiotic, antiviral, RNA, and any combination thereof.

21. The 3D printed hydrogel according to claim 20, wherein the bioactive molecule is collagen.

22. The 3D printed hydrogel according to claim 1, further including a cell culture medium.

23. A method of preparing a drop on demand 3D printed hydrogel, the method comprising:
providing a polymer bio-ink comprising a maleimide containing polymer selected from a PEG maleimide, a gelatin maleimide, or a combination thereof;

providing an activator comprising a bis-thiol containing cross-linking agent having at least two thiol functional groups;

printing the polymer bio-ink and the activator by drop on demand printing, wherein a drop of polymer bio-ink is applied to a substrate followed by a drop of activator to form the hydrogel, or a drop of activator is applied to the substrate followed by a drop of polymer bio-ink to form a hydrogel droplet;

repetitive deposition of a drop of the polymer bio-ink and the activator onto the hydrogel droplet to form a 3D printed hydrogel;

wherein the hydrogel is formed within 1 second or less from the printing of the polymer bio-ink and the activator, with NaOH or other suitable base to adjust pH of the polymer or cross-linking agent.

24. The method according to claim 23, further comprising providing cells during printing to form a 3D printed hydrogel containing cells.

25. The method according to claim 24, wherein the cells are present in the polymer bio-ink, in the activator, both in the polymer bio-ink and the activator, or in a separate medium prior to 3D printing.

26. The method according to claim 23, wherein the polymer bio-ink, the activator, or both the polymer bio-ink and the activator are adjusted to about pH 7.4 prior to printing.

27. The method according to claim 26, wherein the pH is adjusted using NaOH.

28. A cell assay comprising a 3D printed hydrogel containing cells according to claim 14.

* * * * *

```
                        SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 1

Gly Cys Ile Pro Val Ser Leu Arg Ser Gly Cys Gly
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 2

Gly Cys Arg Asp Gly Pro Gln Gly Ile Trp Gly Gln Asp Arg Cys Gly
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 3
```

-continued

```
Gly Cys Arg Asp Pro Leu Gly Leu Asp Arg Cys Gly
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 4

Gly Cys Arg Asp Glu Ala Pro Leu Lys Gln Asp Arg Cys Gly
1               5                   10
```